US009925035B2

(12) United States Patent
Balasubramanian et al.

(10) Patent No.: US 9,925,035 B2
(45) Date of Patent: Mar. 27, 2018

(54) IMPLANTED PASSIVE ENGINEERING MECHANISMS AND METHODS FOR THEIR USE AND MANUFACTURE

(71) Applicant: Oregon State University, Corvallis, OR (US)

(72) Inventors: Ravi Balasubramanian, Corvallis, OR (US); Taymaz Homayouni, Corvallis, OR (US); Francisco Valero-Cuevas, La Crescenta, CA (US)

(73) Assignee: Oregon State University, Corvallis, OR (US)

( * ) Notice: Subject to any disclaimer, the term of this patent is extended or adjusted under 35 U.S.C. 154(b) by 166 days.

(21) Appl. No.: 14/725,971

(22) Filed: May 29, 2015

(65) Prior Publication Data

US 2015/0342722 A1 Dec. 3, 2015

Related U.S. Application Data

(60) Provisional application No. 62/005,707, filed on May 30, 2014.

(51) Int. Cl.
*A61F 2/08* (2006.01)

(52) U.S. Cl.
CPC ........ *A61F 2/08* (2013.01); *A61F 2220/0075* (2013.01); *A61F 2250/0071* (2013.01); *A61F 2250/0073* (2013.01)

(58) Field of Classification Search
CPC ................................ A61F 2/08; A61F 2/0811
USPC .......................................... 623/13.11–13.18
See application file for complete search history.

(56) References Cited

U.S. PATENT DOCUMENTS

| 8,231,158 | B2 | 7/2012 | Dollar et al. | |
| 2008/0188936 | A1* | 8/2008 | Ball | A61B 17/1146 623/13.14 |
| 2008/0195204 | A1* | 8/2008 | Zhukauskas | A61F 2/08 623/13.14 |
| 2008/0200992 | A1* | 8/2008 | Koob | A61F 2/08 623/23.72 |
| 2011/0118837 | A1 | 5/2011 | Delli-Santi et al. | |
| 2011/0160749 | A1 | 6/2011 | Gordon et al. | |

(Continued)

OTHER PUBLICATIONS

Balasubramanian, et al., "Implanted Miniature Engineering Mechanisms in Tendon-Transfer Surgery Improve Robustness of Post-Surgery Hand Function," *Hamlyn Symposium on Medical Robotics* (2 pages), London, UK, Jun. 22-25, 2013.

(Continued)

*Primary Examiner* — Suzette J Gherbi
(74) *Attorney, Agent, or Firm* — Klarquist Sparkman, LLP

(57) ABSTRACT

Implantable passive engineered mechanisms and a method for implanting such devices in a subject are described. The implantable passive engineered mechanism may be made of or comprise a biocompatible material and is appropriately sized for implantation in a subject. Exemplary implantable passive engineered mechanisms may be selected from a strut, a pulley, a lever, a compliant mechanism, a scissor lift, a tendon network, springs, planetary gears, rigid or soft hydraulics, a linkage system, a cam/clutch system, or combinations thereof. In some embodiments the system comprises plural inserts, such as pulleys, levers, and/or tendon networks. Plural inserts may be arranged hierarchically to distribute force differentially from an input to one or more outputs.

19 Claims, 23 Drawing Sheets

(56) References Cited

U.S. PATENT DOCUMENTS

| | | | |
|---|---|---|---|
| 2011/0202002 A1* | 8/2011 | Gordon | A61B 17/0401 604/103.13 |
| 2014/0067061 A1* | 3/2014 | Kubiak | A61B 17/08 623/13.14 |
| 2014/0148850 A1* | 5/2014 | DiMatteo | A61B 17/0401 606/232 |
| 2014/0257349 A1* | 9/2014 | Sudekum | A61F 2/0811 606/151 |
| 2014/0316463 A1* | 10/2014 | Shino | A61B 17/0401 606/232 |
| 2015/0051700 A1* | 2/2015 | Collette | A61B 17/0401 623/13.14 |
| 2015/0127103 A1* | 5/2015 | Seedhom | A61F 2/0063 623/13.14 |
| 2015/0201924 A1* | 7/2015 | Gordon | A61B 17/0401 606/144 |
| 2015/0223926 A1* | 8/2015 | Foerster | A61B 17/0401 606/232 |
| 2015/0245841 A1* | 9/2015 | Linder | A61B 17/064 606/151 |
| 2015/0366672 A1* | 12/2015 | DelSignore | A61B 17/0401 623/21.15 |
| 2016/0151165 A1* | 6/2016 | Fallin | A61F 2/08 623/13.11 |

OTHER PUBLICATIONS

Homayouni et al., "Modeling Implantable Passive Mechanisms for Modifying the Transmission of Forces and Movements between Muscle and Tendons," *IEEE Transactions of Biomedical Engineering* 62(9):2208-2214, Sep. 2015.

Hunter Implants, Ortotech, http://ortotech.com/.

Labview National Instrument, http://www.ni.com/labview/.

Martin et al., "A Passive Implant that Scales Muscle Force in Knee-Replacement Surgery," Sep. 1, 2014.

Optitrack Natural Point, http://www.naturalpoint.com/optitrack.

Su et al., "A Device for Zone II Flexor Tendon Repair. Surgical Technique," *The Journal of Bone and Joint Surgery* [Am] 88-A Supplement 1:37-49, 2006.

Sueda, "Strand-based Musculotendon Simulation of the Hand," *Thesis for Doctor of Philosophy*, submitted to the University of British Columbia, Section 6.4, pp. 81-87, Dec. 2010.

\* cited by examiner

IMPLANTED PASSIVE ENGINEERING MECHANISMS AND METHODS FOR THEIR USE AND MANUFACTURE

CROSS REFERENCE TO RELATED APPLICATION

The present application claims the benefit of the earlier priority date of U.S. provisional application No. 62/005,707, filed on May 30, 2014, which is incorporated herein by reference.

FIELD

This invention relates generally to implantable mechanisms and methods for using such mechanisms and their manufacture.

BACKGROUND

Tendon-transfer surgeries are performed to partially restore musculoskeletal function for a variety of conditions such as stroke, paralysis, nerve, muscle, brain, or spinal trauma, and congenital disorders. Surgical techniques for restoring or improving musculoskeletal function typically involve attaching the muscles and tendons to a bone or muscle using sutures. In at least fifteen types of hand tendon-transfer surgeries, a single donor muscle is directly sutured to multiple recipient tendons. The suture couples the movement of the muscle and the tendons to replicate prior function, but cannot preferentially enhance, scale, or distribute a muscle's force and movement across the tendons. This leads to limited post-surgery musculoskeletal function and surgical choices.

Prior work has explored three primary types of medical devices for restoring or enhancing musculoskeletal function: (1) rigid passive implants that directly attach to bones, such as joint replacement implants or implants for holding bones together after fractures; (2) implants that secure two biological tendons, such as tenofix and Otho-Hunter implants, or biological tendons to bone, such as the Orthocoupler implant; (3) external devices that are body-powered or externally powered, such as prostheses for lost body parts, orthoses for correcting misalignments, or exoskeletons for assisting in movement.

Two of the most common types of surgery for the improvement of musculoskeletal function are tendon-transfer surgery and knee-replacement surgery. Each of these conditions severely affects hand function and prevents a person from performing even basic activities of daily life. Tendon-transfer surgery restores lost hand function by re-routing one or more tendons from the affected muscle and suturing them to a functioning muscle. For example, in tendon-transfer surgery for high median-ulnar palsy, a severe condition that disables all four flexor digitorum profundus (FDP) muscle bellies, all four FDP tendons are sutured directly to a functioning muscle, such as the extensor carpi radialis longus (ECRL). The ECRL muscle, which is a wrist extensor, has only one muscle belly. Accordingly, when the ECRL contracts, all four fingers curl inward simultaneously and equally. As a result, if one finger makes contact with an object during the grasping process while the other fingers are still closing, further ECRL contraction to close the remaining fingers forces the finger that has already made contact to curl further and slip on the object. Furthermore, the muscle may have to stretch the tendon of the finger that has already made contact in order to flex the other fingers, increasing muscle force requirement. Overall, this deleteriously affects grasping capability and limits the activities of daily living.

A key problem with the current surgical procedure is that the suture couples the movement of all four fingers, leading to poor hand function in fundamental tasks such as grasping of objects since the fingers cannot adapt naturally to the object shape. Specifically, the coupled finger movement leads to (1) incomplete and weak grasps, (2) greater muscle force requirement since the muscle has to isometrically stretch tendons to flex the other fingers once one finger makes contact, (3) uneven tendon stretching, which results in even more unbalanced finger movement over time, and (4) large unbalanced forces on the object during the grasping process (observed in robotic hands). Also, significant challenges arise in current tendon-transfer surgery due to choosing from a limited set of donor muscles. If the surgeon makes even a 5% error in tensioning the tendons finger movement would be either premature or delayed during the grasping process.

In knee-replacement surgery, the knee joint is replaced with a single-degree of freedom artificial joint that mimics the knee's kinematics. However, knee joint strength typically decreases by 30% following surgery. Such strength loss impedes daily activities such as chair rising and stair climbing.

Accordingly, there is need in the art to develop mechanisms and methods for their use for improving musculoskeletal function. There is a particular need to develop mechanisms and methods that allow for more preferential enhancement, scaling, and/or distribution of a muscle's force and movement across the tendons.

SUMMARY

Certain disclosed embodiments concern an implantable passive engineered mechanism. The mechanism may comprise a biocompatible materials, or at least a portion thereof may be coated with a biocompatible material.

For certain embodiments an implantable passive engineered mechanism preferentially enhances, scales, and/or distributes an input force and movement across output tendons. The input force may be provided by muscle, tendon, and/or bone. Mechanisms may be used to scale force inputs and outputs from a muscle to a tendon, to differentially distribute force inputs across two or more tendons, or some combination thereof. Implantable passive engineered mechanisms may, for example, be used to improve grasping strength and function in hands that have suffered a loss of finger function, or to increase knee-joint torque after knee surgery. A key aspect of grasping is the ability to overcome uncertainty in the grasping of irregular objects by controlling individual finger flexion. Subjects with finger impairments may not have individual control of flexion or proper tactile feedback. Some disclosed embodiments address this problem by enabling the fingers to individually adapt to the object's shape using less actuation force; unused muscle force may be used to increase grip strength after the fingers close on the object. Relative to current embodiments wherein the tendons are sutured directly to the input muscle, the implanted mechanisms lead to better finger movement by facilitating the ability of digits to enclose an object even when the finger tendons are actuated by just one muscle.

In one example, the disclosed mechanism is a strut that is coupled to and separates tendons on either side. The mechanism used to separate the tendons may also have a different shape, such as a triangular insert where the tendons can be coupled to two sides of the triangle and then connect to an input force. This separation of the tendons using a mechanism provides several advantages, such as differential application of force across the tendons.

In another example, the mechanism is coupled directly in line with the input force and has multiple outputs that allow it to be coupled to multiple output tendons. In some examples, the mechanism is a soft tendon network made from flexible material that is connected on one end to the input force and on the other end to two or more tendons. Because the material is flexible the mechanism may be anchored to the subject's bone. Certain specific disclosed tendon network embodiments include: a soft parallel tendon network made of artificial or biological tendon; a polymeric matrix; a triangular tendon network; plural tendon networks; and/or hierarchical plural tendon networks. In a particular embodiment of a hierarchical tendon network, three triangular tendon networks are arranged hierarchically with the first vertex of the first network being effectively coupled to the input muscle, and the second and third vertices of the first network being coupled to the first vertices of the second and third networks, and where the second and third vertices of the second and third tendon networks are connected to output tendons.

In other examples, the mechanism is a pulley or a system of pulleys that include at least one pulley cable. In a particular example, a singular pulley is anchored to an output bone or tendon, and a pulley cable is coupled to an input muscle on a first end and an anchor bone on a second end. In a two pulley example, the two pulleys may be linked by a single pulley cable, which is anchored to a bone at a first end, and anchored to an output at a second end, and the body of the second pulley is connected to the input force. In another two pulley example, a first end of a first pulley is anchored to a bone and the second end is anchored to the body of the second pulley, a third end is anchored to a bone, a fourth end is connected to an input force, and the body of the first pulley is connected to an output tendon. In a three pulley system, the pulleys may be arranged hierarchically, so that they may be implanted in line with an input force and output tendons, or they may be arranged with two of the pulleys anchored to bone with pulley cables connecting the pulleys. In one example, three pulleys are arranged hierarchically, with a first pulley connected to an input muscle and to second and third pulleys, which are connected to four output tendons. In another example, the first and second pulleys share a pulley cable, the first end is anchored, such as to a bone, and the second end is connected to the third pulley, which has a pulley cable with one end anchored and the second end connected to an output tendon. The second pulley is also connected to the input muscle.

In other examples, the mechanism is a lever or system of levers. A single lever can be used to scale force(s) and lever systems can be used to spread force(s) and movement(s) differentially over multiple tendons. Levers can be anchored to bone. Levers can also be arranged hierarchically in line with an input force and output tendons. The location of the input force or the connections between multiple levers can be selected specifically to vary the output force.

Other disclosed exemplary implantable passive engineered mechanisms include: (1) a trapezoidal compliant mechanism having a first portion effectively coupled to an input muscle and a second portion effectively coupled to an output tendon; (2) a scissor mechanism, with particular examples of the scissor mechanism having a first portion anchored, such as to a bone, and a second portion received in a slot defined in a bone and having a second end effectively coupled to an input muscle and where the scissor mechanism is effectively coupled to an output tendon at a selected position between the two ends; (3) a disc having an arc for receiving a stud and two pulleys, each having a body and a pulley cable comprising a first and a second end, wherein the stud is effectively coupled to the input muscle and the first and second ends of each pulley cable are effectively coupled to output tendons; (4) planetary gears; (5) a linkage system; (6) a rigid or soft hydraulic system; or (7) a cam/clutch system.

Disclosed mechanisms may be used separately or in combination. For example, a system may comprise plural mechanisms, for example, a lever and a pulley, or a lever, a pulley, and a strut.

The mechanism may be made of any suitable material as would be understood by a person of ordinary skill in the art. For example, certain enclosed embodiments are made of polymeric materials, metals, alloys, or combinations thereof. Certain exemplary polymeric materials include polyalkylenes, polyesters, or elastomers. Particular examples include ultra-high molecular weight polyethylene, nylon, polyester/PET, or poly-paraphenylene terephthalate. Exemplary metals include titanium, tantalum, or combinations thereof. Exemplary alloys include stainless steel. The mechanism may also be coated with a biocompatible coating, including but not limited to, a covalently grafted non-fouling layer or a surface immobilized brush of chemicals (in one example, sulfobetaine), or enclosed in a biocompatible sheath.

One or more of the disclosed mechanisms may be implanted in a subject. The implanted mechanism may allow the subject to preferentially enhance, scale, and/or distribute a muscle's force and movement across one or more tendons. The mechanisms may be implanted using existing methods of implantation, including but not limited to: sutures, bone screws, bone anchors, or weaving.

In a particular example, a subject may have high median ulnar palsy which causes a loss of hand function. The implanted mechanisms may be used to connect the ECRL muscle to the FDP tendons of the fingers allowing the subject to have an increased ability to adapt finger movement and finger force individually in order to grasp objects. The mechanisms allow the fingers to move with increased individuality, instead of moving in a coupled motion. In another particular example, the subject may have experienced a loss of knee strength after a knee replacement surgery. Loss of knee strength affects everyday tasks, such as stair climbing and chair rising. Implantation of a passive engineered mechanism allows for force scaling from the quadriceps muscle to the patella. The mechanisms have the potential to bring a paradigm shift in reconstructive orthopedic surgery by customizing the transmission of forces and movements within the subject based on the subject's requirements.

In another particular example, wherein a subject has severe total paralysis and no muscles are available to serve as an input force, tenodesis may be performed. Tenodesis involves connecting extensor and flexor tendons of the hand to a bone in such a way that during the extension of the wrist the flexors are tightened and the extensors relaxed, thereby producing finger flexion. The implanted passive engineered mechanisms may use tenodesis as their input force.

The foregoing and other objects, features, and advantages of the invention will become more apparent from the following detailed description, which proceeds with reference to the accompanying figures.

DETAILED DESCRIPTION

I. Introduction

Figure 1:
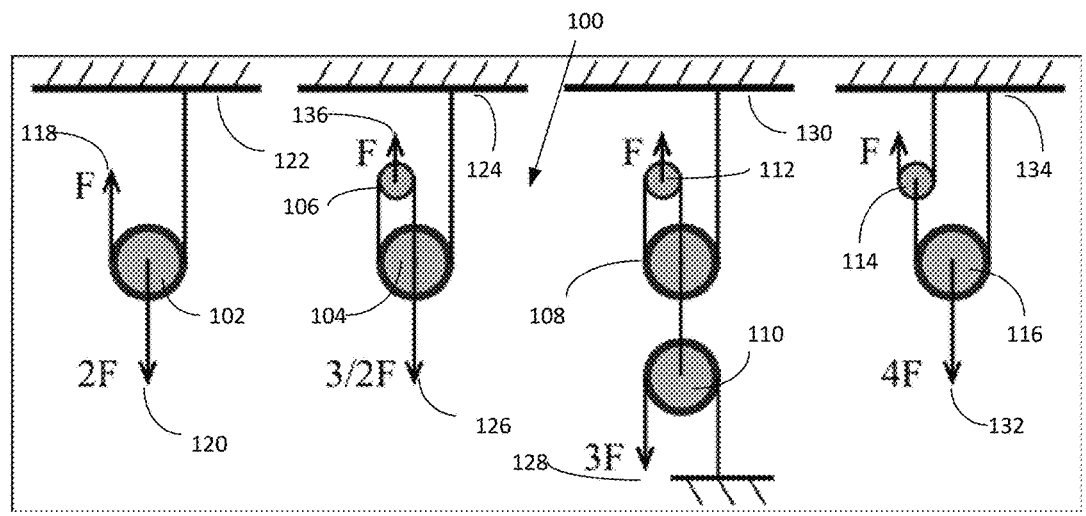
FIG. 1 is a schematic plan view illustrating various embodiments of pulley/pulley systems for use in accordance with embodiments of the present invention.

Passive engineered mechanisms may be implanted at any of various locations in a subject. For example, in some embodiments they are used for tendon-transfer surgery and in other embodiments in general orthopedic surgery, to improve the functional attachment of muscles to tendons and bones. Common locations for implantation include, but are not limited to: (1) the hand, wherein the four tendons of the fingers (the flexor digitorum profundus, FDP, tendons) are coupled to the extensor carpi radialis longus (ECRL), the muscle of the forearm; (2) the elbow, wherein the biceps brachii is coupled to the ulna or the radius; and (3) the knee, wherein tendons are used to couple the large muscles of the thigh, such as the vastus medialis, vastus intermedius, and vastus lateralis, to the patella.

II. Definitions

The following explanations of terms and abbreviations are provided to better describe the present disclosure and to guide those of ordinary skill in the art and practice of the present disclosure.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the detailed description and the claims.

As used herein, "comprising" means "including" and the singular forms "a" or "an" or "the" include plural references unless the context clearly dictates otherwise.

The term "or" refers to a single element of stated alternative elements or a combination of two or more elements, unless the context clearly indicates otherwise.

In order to facilitate review of the various embodiments of the disclosure, the following explanations of specific terms are provided:

Biocompatible:

A substantially non-toxic material in vivo that is not substantially rejected by the patient's physiological system (e.g., is nonantigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of subjects, will not cause a significantly adverse reaction or response. Furthermore, biocompatibility can be affected by other contaminants such as prions, surfactants, oligonucleotides, and other agents or contaminants. The term "biocompatible material" refers to a material that does not cause toxic or injurious effects on a tissue, organ, or graft. Examples, without limitation, of biocompatible materials include: titanium, ultra-high molecular weight polyethylene, polyvinylidene fluoride, and elastomers.

Coat:

As used herein, "coat," "coating," "coatings," and "coated" are forms of the same term referring to materials and process for making a material where a first substance or substrate surface is at least partially covered or associated with a second substance. The first and second substances may be, but are not required to be, different. Further, when a surface is "coated" as used herein, the coating may be effectuated by any chemical or mechanical bond or force, including linking agents. The "coating" need not be complete or cover the entire surface of the first substance to be "coated." The "coating" may be complete as well (e.g., approximately covering the entire first surface). There can be multiple coatings and multiple substances within each coating. The coating may vary in thickness or the coating thickness may be substantially uniform. Coatings contemplated in accordance with the present disclosure include, but are not limited to, biocompatible coatings, medicated coatings, drug-eluting coatings, drugs or other compounds, pharmaceutically acceptable carriers and combinations thereof, or any other organic, inorganic or organic/inorganic hybrid materials. Examples of biocompatible coatings include, but are not limited to: polyurethane, phosphorylcholine, bovine submaxillary mucin coatings, covalently grafted non-fouling layers, or surface immobilized brushes of chemicals including but not limited to sulfobetaine.

Subject:

An animal or human subjected to a treatment, observation or experiment.

III. Descriptions of Implantable Mechanisms

Disclosed herein are various embodiments of implantable passive engineered mechanisms. Disclosed embodiments are useful to, for example, improve the functional attachment of muscles to tendons and bones by modifying the transmission of forces and movement inside the body.

Certain disclosed embodiments are force scaling implants that are used to connect a single input force to a single output force and to allow for the input force to be scaled up or down to create a stronger or weaker output force. The input force may be an active muscular or tendon force, or a passive input, for example tenodesis. In tenodesis the tendon can be anchored to a bone or other fixed structure such that the rotation of the joint distal to the anchor lengthens the path of the mechanism, producing a force.

FIG. 1 illustrates exemplary implantable pulley systems. Pulley 102 may attach to a tendon or muscle at 118 and anchor to bone at 122. The pulley 102 doubles the input force at 120.

A second pulley system comprises pulleys 104 and 106. Pulleys 104 and 106 are anchored at 124, and are connected to tendon or muscle at 136 and to tendon or muscle at 126. Pulleys 104 and 106 increase input force 136 by 3/2 before output 126.

The third exemplary pulley system comprises pulleys 108, 110, and 112. The illustrated three pulley system anchors in two places, 128 and 130. This illustrated pulley configuration allows the output force to exceed the input force by a factor of 3.

The fourth pulley system comprises two pulleys 114 and 116. Pulleys 114 and 116 are each anchored on one side to the same bone 134. This illustrated configuration allows the output force to exceed the input force by a factor of 4.

Figure 2:
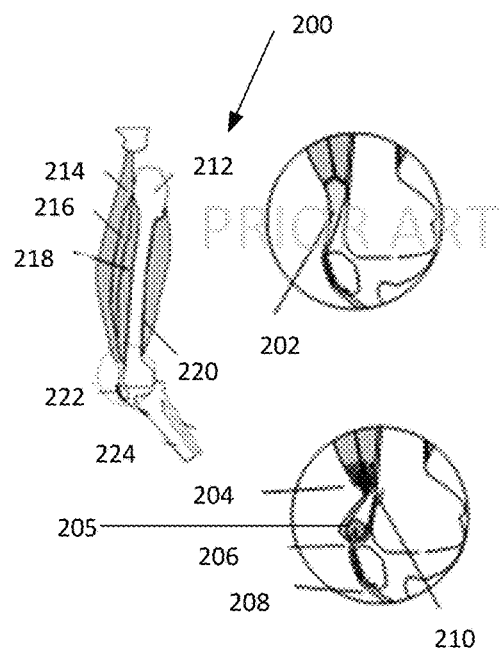
FIG. 2 is a side schematic view illustration of a knee with cutouts showing the traditional suture procedure and one embodiment of an implanted pulley mechanism.

In some embodiments, a pulley would be used for knee-joint surgery. FIG. 2 illustrates the musculature and skeletal structure of the human knee. 214 is the Rectus Femoris, 216 the Vastus Medialis, 218 the Vastus Intermedialis, 220 the Vastus Lateralis, 222 the patella, and 224 the tibia. 202 is a cutout illustrating the current suture-based technique for knee-joint surgery. The second cutout illustrates the first pulley configuration from FIG. 1 implanted in a human knee. Pulley 205 is anchored to bone at 210 and to the muscles of the thigh at 204. The quadriceps tendon, 206, is sutured to the patellar ligament 208.

Figure 3:
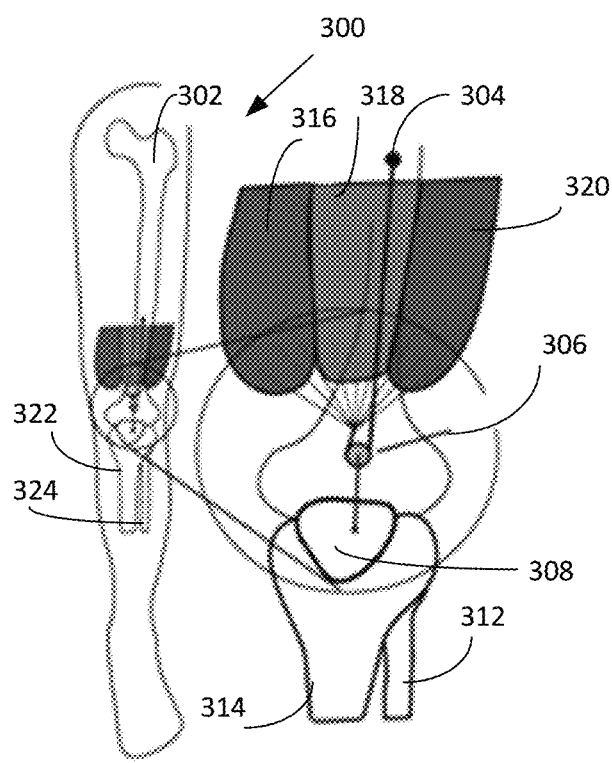
FIG. 3 is a schematic edge view illustrating one embodiment of a pulley mechanism implanted in a human knee.

FIG. 3 illustrates a singular pulley 306 implanted in a human knee. 304 is the anchor point wherein the cable through pulley 306 is affixed to the femur 302. Pulley 306 is also anchored to the patella 308. The Vastus Medialis (316), Vastus Intermedius (318), and Vastus Lateralis (320) all connect to pulley 306 and supply the necessary input force.

Figure 4:
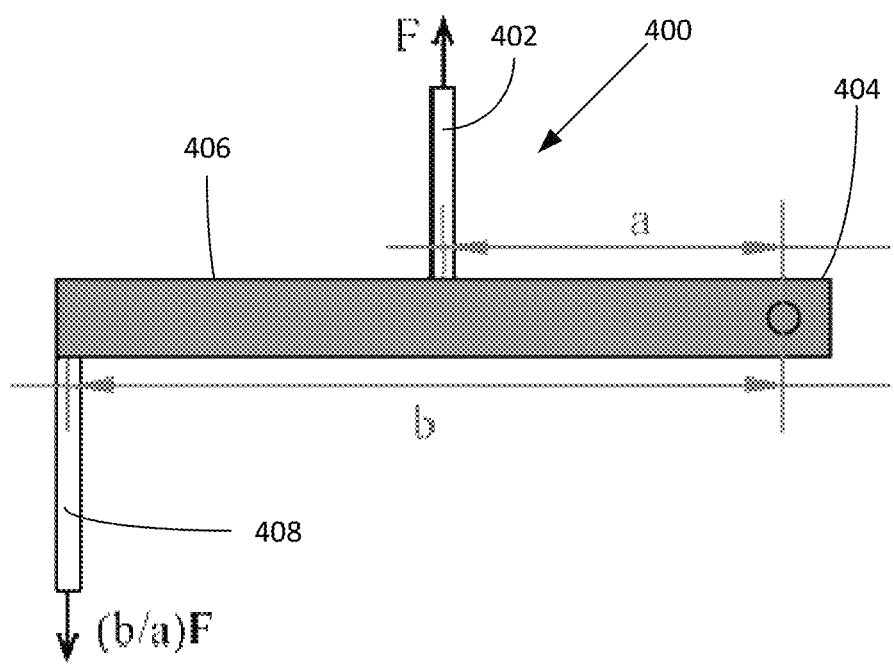
FIG. 4 is a schematic view illustrating one embodiment of a lever for use in accordance with embodiments of the present invention.

FIG. 4 illustrates an embodiment of an implantable passive engineered mechanism comprising a lever 406. Lever 406 is anchored to bone 404. The length of lever 406 and the position of the input force, 402, along the length of the lever determine output force 408. 402 is the location where lever 406 would be connected to an input force, and 408 is the location where lever 406 would be connected to an output tendon.

Figure 5:
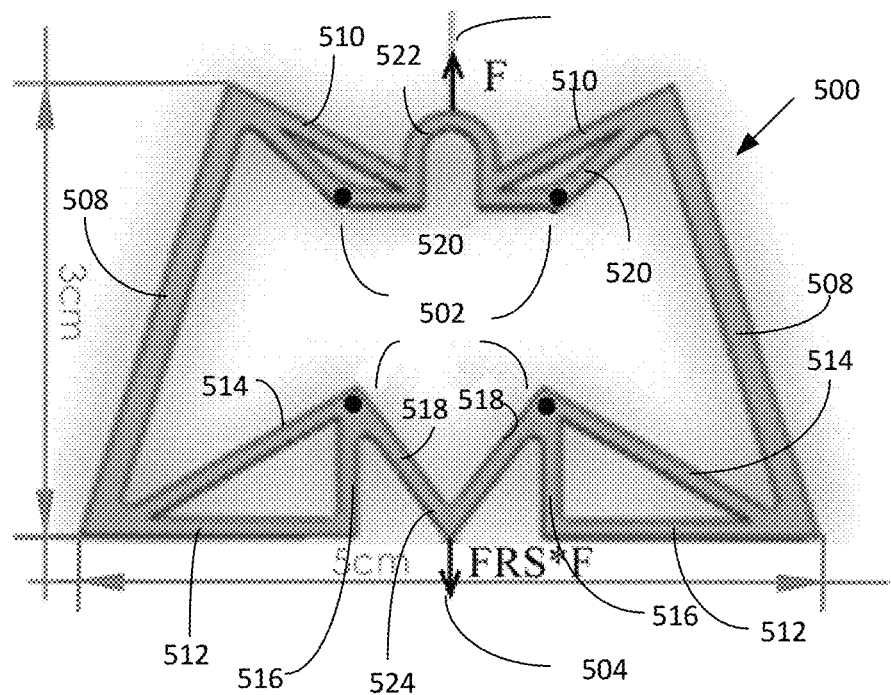
FIG. 5 is a schematic plan view illustrating one embodiment of a compliant mechanism for use in accordance with embodiments of the present invention.

FIG. 5 illustrates an embodiment comprising compliant mechanism 500. Mechanism 500 is a unitary compliant device having multiple integral components 508, 510, 512, 514, 516, 518, and 520. Segments 510 and 520 further define a U-shaped input 522. Segments 512, 514, 516, and 518 define triangular output segment 524.

FIG. 5 also provides exemplary dimensions (3 cm×5 cm) for implantation in a subject. Compliant mechanism 500 is anchored to bone, using bone screws, at 4 anchor points 502. Input force 506 can be adjusted to scale with the size of the mechanism to determine the strength of the output force 504. The illustrated passive engineered mechanism defines a closed structure, which allows fewer fibrosis opportunities or moving parts failing or impairing surrounding tissue structures.

Figure 6:
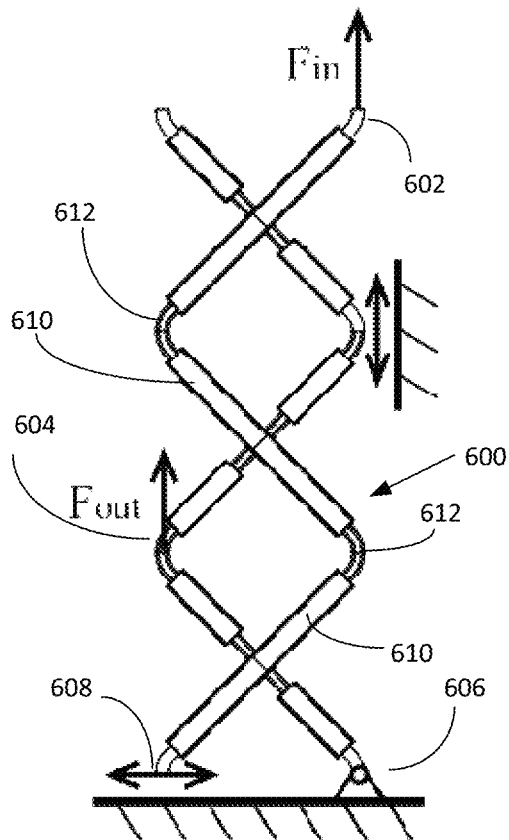
FIG. 6 is a schematic view illustrating one embodiment of a scissor lift mechanism for use in accordance with embodiments of the present invention.

FIG. 6 illustrates an embodiment comprising a scissor lift mechanism 600. Mechanism 600 comprises plural connected segments 610. Segments 610 are coupled at pivot positions 612 that allow mechanism 600 to extend as constrained by application of extension or contraction forces. Passive engineered mechanism 600 is anchored to the bone at 606. A groove cut may be made in the bone to receive end 608. End 608 can move back and forth in the groove when the scissor lift 600 extends and contracts. The input force, a muscle, connects at 602. 604 receives the output force.

Certain illustrated embodiments are differential action implants that connect a single muscle to multiple tendons. This arrangement allows for improved preferential enhancement, scaling, and/or distribution of an input's force and movement across the tendons. Unlike force scaling mechanisms, differential action implants may not be anchored to a bone.

Figure 7:
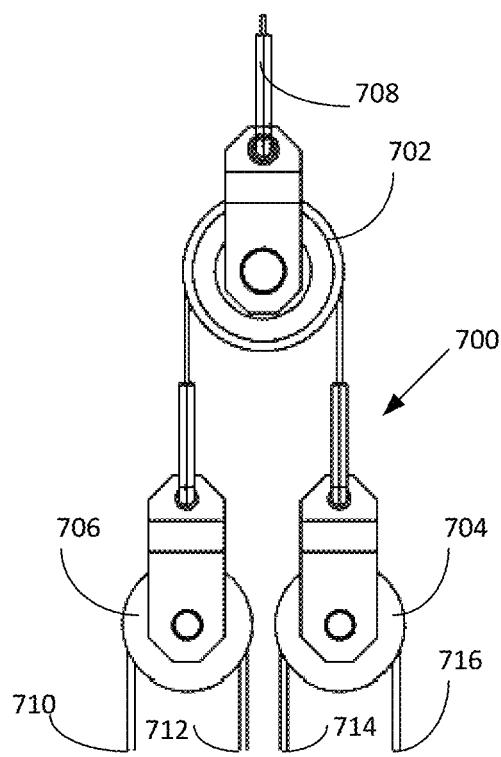
FIG. 7 is a schematic plan view illustrating one embodiment of a hierarchical pulley system for use in accordance with embodiments of the present invention.

FIG. 7 illustrates an embodiment comprising a hierarchical pulley system 700 comprising multiple pulleys 702, 704, and 706 acting in combination. A triangular configuration is defined between pulley 702 and pulleys 704 and 706. System 700 is effectively coupled to an input force, such as muscle, at 708 and to output tendons at 710, 712, 714, and 716. System 700 facilitates force differentiation from a muscle to tendons.

Figure 8:
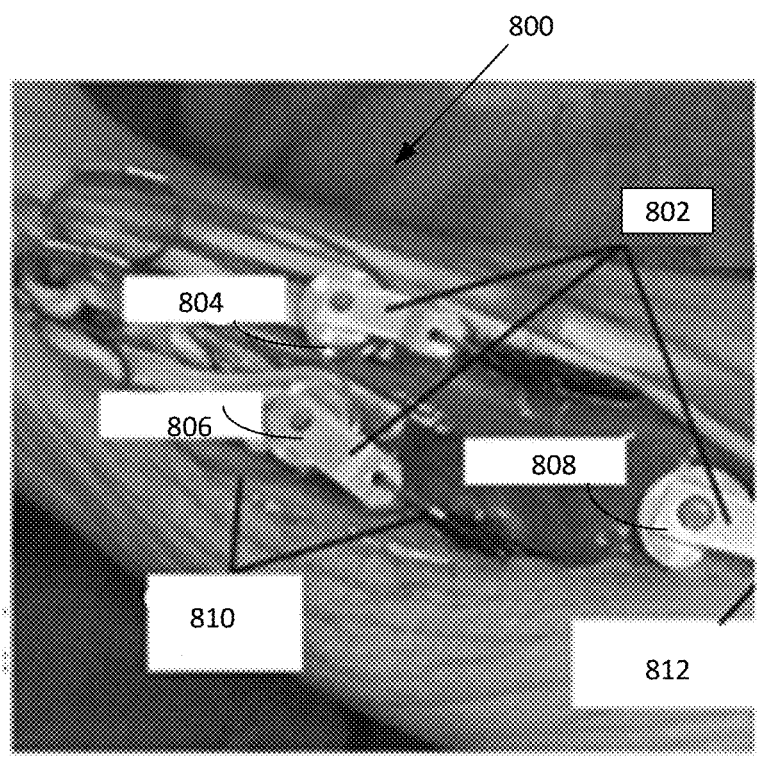
FIG. 8 is a photograph of one embodiment of a hierarchical pulley system implanted in the arm of a human cadaver.
Figure 9:
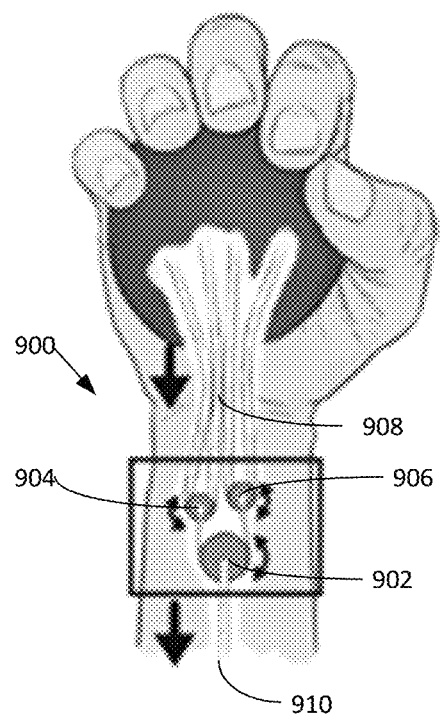
FIG. 9 is a schematic plan view illustrating one embodiment of a hierarchical pulley system implanted in a human arm.

FIG. 8 illustrates a hierarchical pulley system, such as system 700 illustrated in FIG. 7, implanted in the arm of a human cadaver. Pulley 808 has been sutured to the Extensor Carpi Radialis Longus (ECRL) muscle 812. Pulleys 804 and 806 have been connected to the four Flexor Digitorum Profundus (FDP) tendons of the hand using artificial tendons 810. FIG. 9 illustrates how in some embodiments force exerted by the ECRL, 910, is transmitted through the hierarchical pulley system, 902, 904, and 906, to the FDP tendons, 908. This system allows the hand to make a grasping motion and provides fingers a greater range of differentiated motion.

Figure 10:
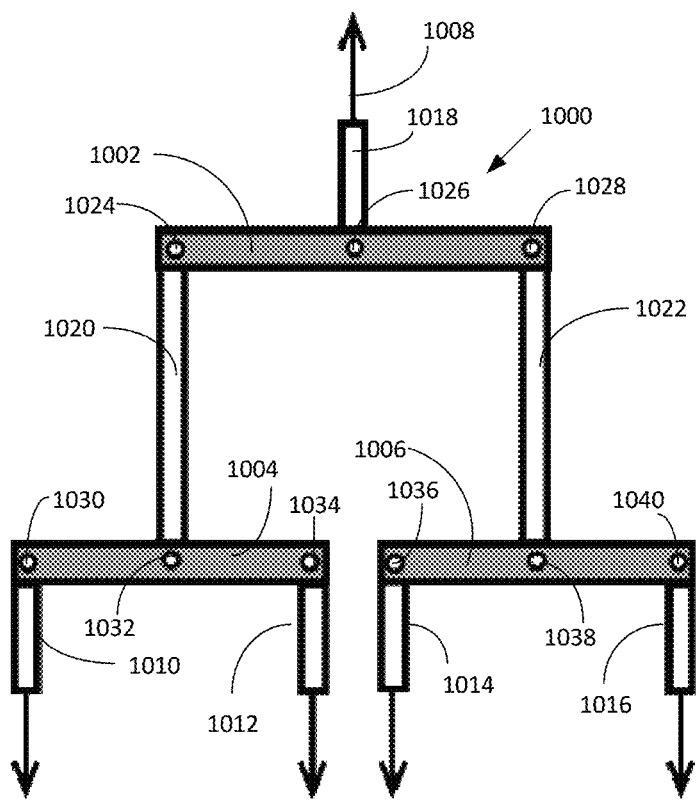
FIG. 10 is a schematic plan view illustrating one embodiment of a hierarchical lever system for use in accordance with embodiments of the present invention.

FIG. 10 illustrates an embodiment comprising a hierarchical lever system 1000. Lever system 1000 comprises three interconnected levers 1002, 1004, and 1006. System 1000 also includes plural connecting artificial tendons 1020 and 1022 that connect lever 1002 at points 1024, 1026, and 1028 to lever 1004 at 1032 and to lever 1006 at 1038. System 1000 connects an input force 1008, such as a muscle, to four output tendons 1010, 1012, 1014, and 1016. The three levers, 1002, 1004, and 1006 provide differential force distribution from the muscle 1008 across the four tendons 1010, 1012, 1014, and 1016. The connection locations between the levers 1002, 1004, and 1006 may be altered to provide variable force distribution.

Figure 11:
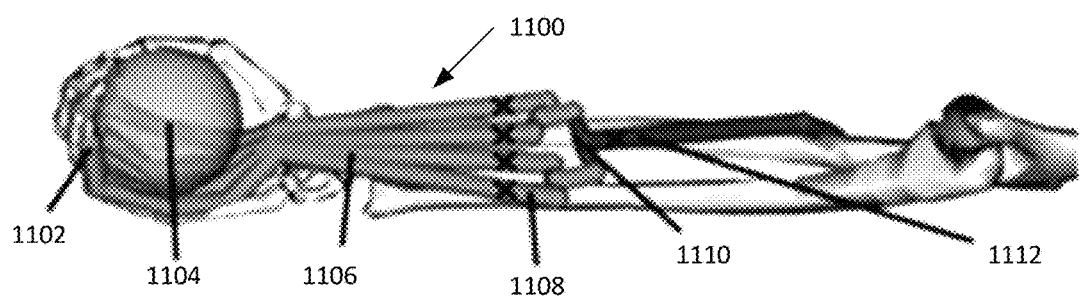
FIG. 11 is a schematic side view illustrating connecting one embodiment of a hierarchical lever system to the tendons and muscles of the human arm.

FIG. 11 schematically illustrates a single lever system implanted in a human arm. ECRL muscle 1112 is connected to the lever 1110. Lever 1110 is connected via artificial tendons 1108 to the natural FDP tendons 1106. FDP tendons 1106 extend all the way to the finger pads 1102. This arrangement allows the fingers to grasp object 1104.

Figure 12:
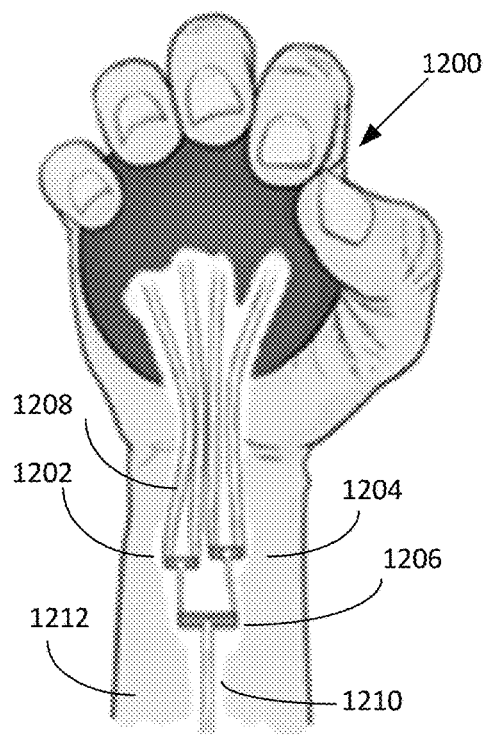
FIG. 12 is a schematic plan view illustrating one embodiment of a hierarchical lever system implanted in a human arm.

FIG. 12 illustrates how an implanted hierarchical lever system comprising levers 1202, 1204, and 1206 implanted in an arm 1212. A force exerted by the ECRL muscle, 1210, is transmitted from lever 1206 to levers 1202 and 1204 and from levers 1202 and 1204 into the FDP tendons 1208. This arrangement allows the hand to make a grasping motion with a greater range of differentiated motion.

Figure 13:
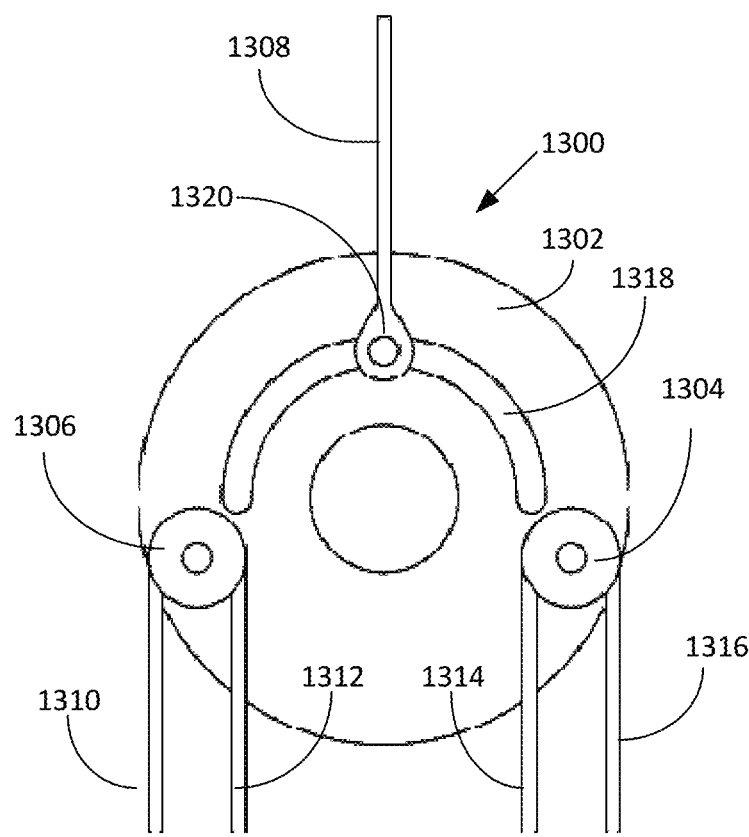
FIG. 13 is a schematic plan view illustrating one embodiment of a hierarchical pulley system comprising a disc and plural pulleys for use in accordance with embodiments of the present invention.

FIG. 13 illustrates an embodiment wherein an input force 1308 is connected to a hierarchical pulley mechanism 1302. System 1300 comprises a substantial circular disc 1302 that defines slot 1318 for receiving stud 1320. End 1320 travels in slot 1318. Circular member 1302 is connected to two pulleys 1304 and 1306, which are in turn connected to four tendons at 1310, 1312, 1314, and 1316. This arrangement allows for a range of differentiated force and motion across tendons 1310, 1312, 1314, and 1316.

Figure 14:
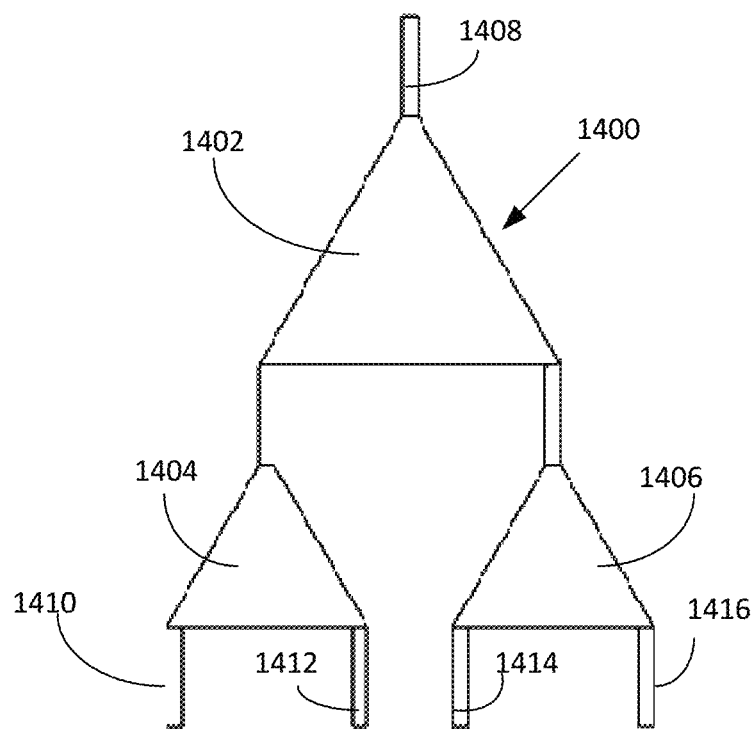
FIG. 14 is a schematic plan view illustrating one embodiment of a hierarchical tendon network system for use in accordance with embodiments of the present invention.

FIG. 14 illustrates an embodiment comprising a hierarchical tendon network mechanism 1400, wherein three triangular networks 1402, 1404, and 1406 comprising artificial tendons are arranged hierarchically. An input force, such as muscle, is connected to tendon network 1402 at 1408, and the biological tendons are connected to tendon network 1404 at 1410 and 1412 and to tendon network 1406 at 1414 and 1416.

Figure 15:
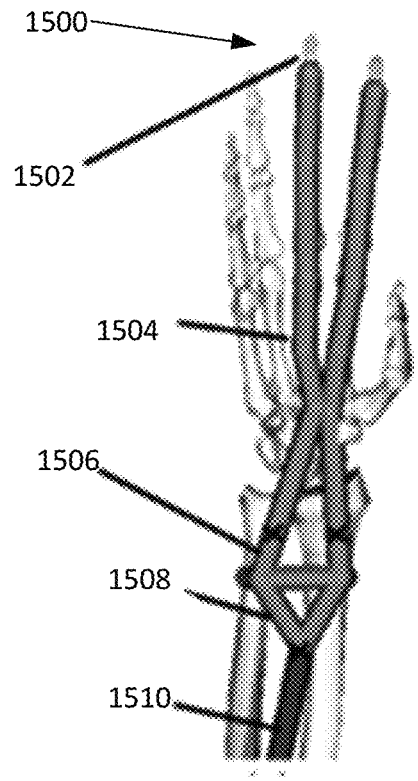
FIG. 15 is a schematic view illustrating one embodiment of a tendon network implanted in a human hand.

FIG. 15 illustrates an embodiment 1500 comprising a tendon network. Tendon network 1500 comprises a tendon network 1508 made of artificial tendon. As with prior embodiments, the tendon networks may define a geometric shape, such as a triangle, to facilitate function upon implantation. Network 1500 is used to attach a muscle 1510 to biological tendons 1504 using artificial tendons and sutures 1506.

Figure 16:
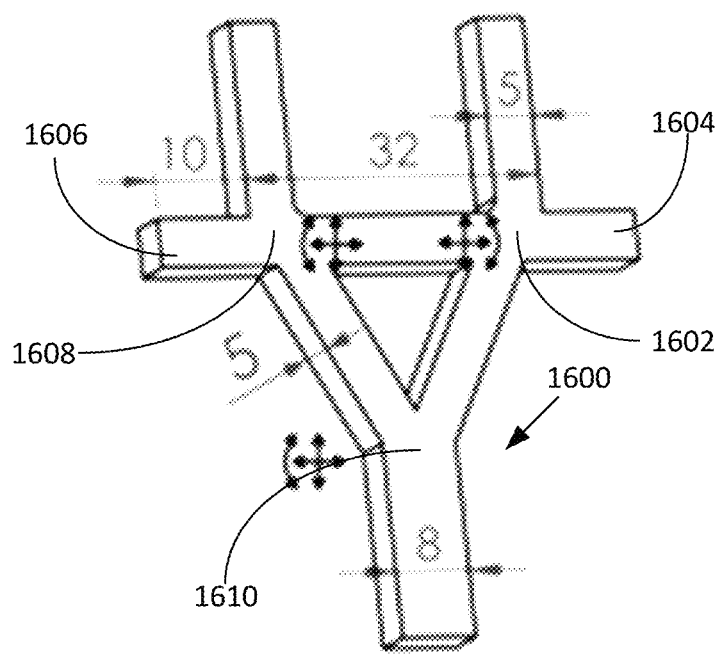
FIG. 16 is a schematic perspective view illustrating one embodiment of an implantable tendon network.

FIG. 16 illustrates a tendon network 1600 that defines an equilateral triangular structure that distributes forces and movements from one input across two outputs equally. Tendon network 1600 is not rigid, and may be anchored to bone(s) at 1604 and 1606. The three triangle vertices 1602, 1608, and 1610, are allowed to slide in a plane parallel to the bones and have three degrees of freedom.

Figure 17:
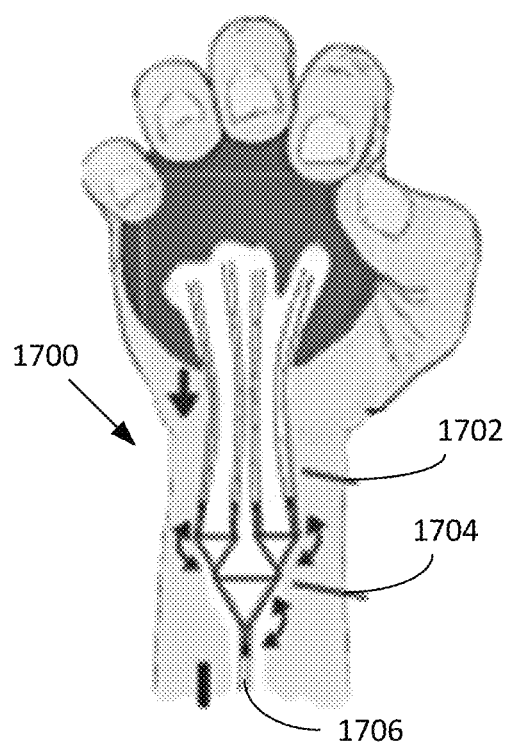
FIG. 17 is a schematic plan view illustrating one embodiment of a hierarchical tendon network system implanted in a human hand.

FIG. 17 illustrates a hierarchical tendon network 1700 implanted in a human arm 1704. Tendon network 1708 is attached to the ECRL muscle of the forearm at 1706. Tendon networks 1710 and 1712 are sutured to the biological tendons 1702.

Figure 18:
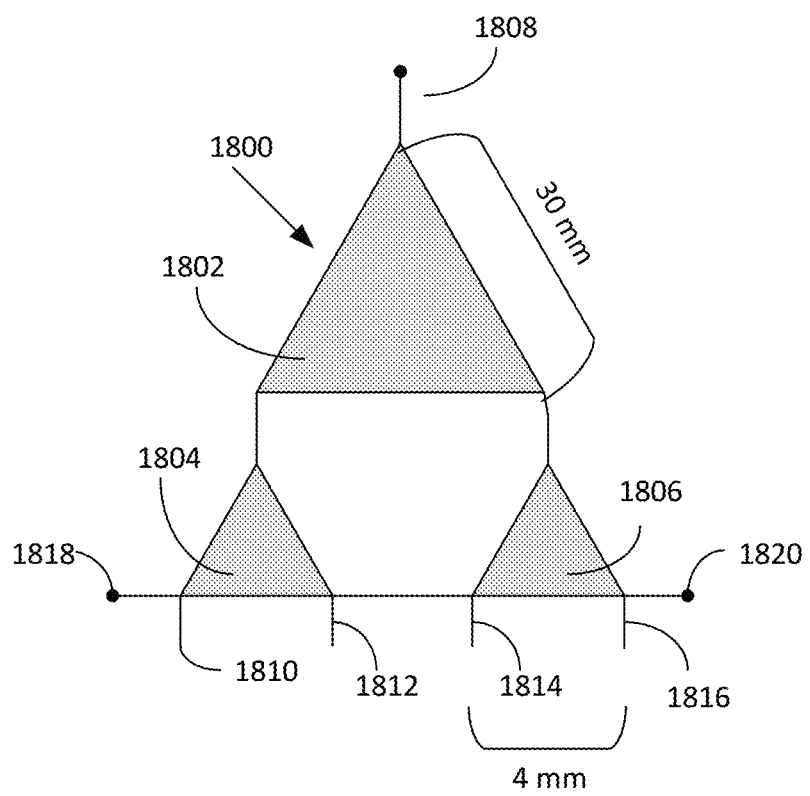
FIG. 18 is a schematic view illustrating one embodiment of a hierarchical tendon network for use in accordance with embodiments of the present invention.

FIG. 18 illustrates a schematic view of a tendon network system 1800 with potential measurements. Tendon network system 1800 comprises tendon networks 1802, 1804, and 1806. 1808 is the muscle input for coupling to tendon network 1802. 1810, 1812, 1814, and 1816 are for tendon outputs. 1818 and 1820 are anchor points. For arm implantation, the anchor points 1818 and 1820 may be the radius and the ulna.

Figure 19:
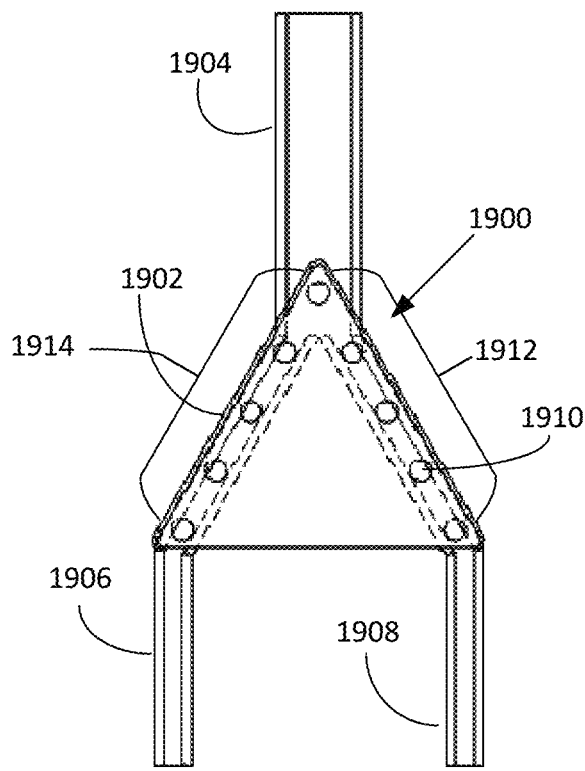
FIG. 19 is a schematic plan view illustrating one embodiment of a triangular tendon insert for use in accordance with embodiments of the present invention.

FIG. 19 illustrates an embodiment 1900 comprising a triangular insert 1902. Embodiment 1900 may be used to connect two output tendons 1906 and 1908, to a third input tendon or muscle 1904. This allows for adaptive movement of the tendons. Triangular insert 1902 contains apertures 1910 on sides 1912 and 1914 which may be used to suture the output tendons to the insert 1902.

Figure 20:
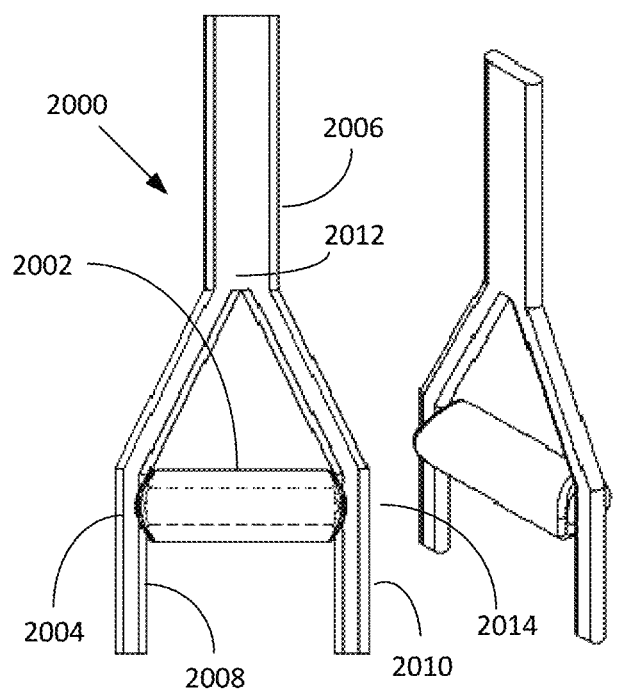
FIG. 20 is a schematic plan view illustrating one embodiment of a strut insert for use in accordance with embodiments of the present invention.
Figure 21:
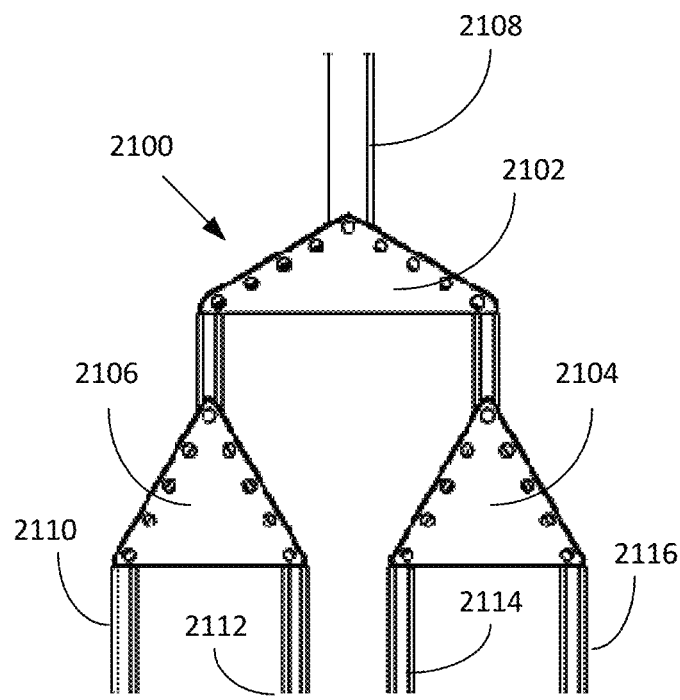
FIG. 21 is a plan view illustrating one embodiment of a hierarchical system of triangular tendon inserts for use in accordance with embodiments of the present invention.

FIG. 20 illustrates an embodiment comprising a strut 2002. Strut 2002 is sized to space two output tendons 2008, 2010 that are attached to the same input force, 2006, at a suture point 2012. Strut 2002 is cylindrical in the illustrated embodiment. Cylindrical strut 2002 is held in place by suturing it to the tendon at points 2004 and 2014. This arrangements defines a triangle shape by the strut 2002 and tendons 2008 and 2010. The triangle shape may rotate as well as translate, which is not possible using current surgical methods. In this embodiment, strut 2002 may comprise a rod or bar designed to resist compression, FIG. 21 illustrates an embodiment comprising triangular inserts 2102, 2104, and 2106. Inserts 2102, 2104, and 2106 are arranged hierarchically so that four output tendons, 2110, 2112, 2114, and 2116 may be attached to the same input force 2108.

Figure 22:
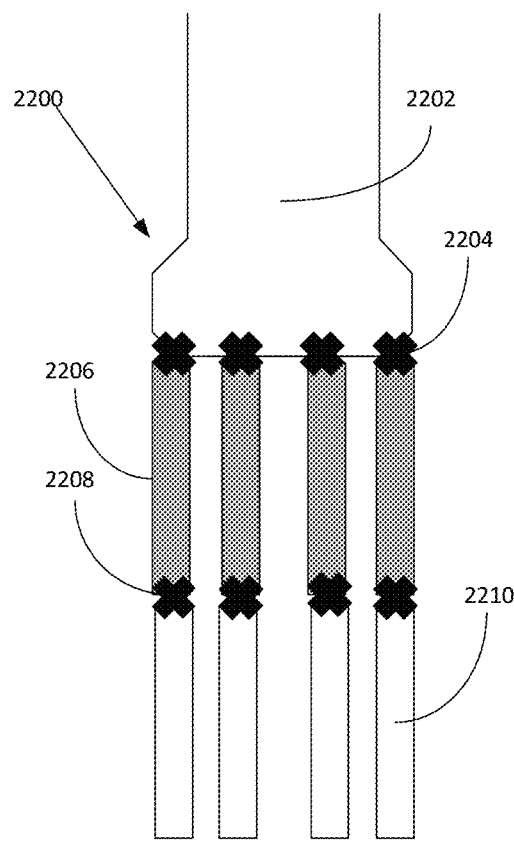
FIG. 22 is a schematic plan view illustrating one embodiment of a parallel soft tendon system for use in accordance with embodiments of the present invention.

FIG. 22 illustrates a soft parallel tendon network 2200. Network 2200 comprises artificial tendons softer than biological tendons. Artificial tendons 2206 are used to connect biological tendons, 2210, to an input force 2202. The artificial tendons are sutured to the input at 2204, and to the biological tendons at 2208. Softer artificial tendon 2206 is in series with an input force 2202 and biological tendon 2210 and thus provides additional compliance for the biomechanical system to counteract finger-joint stiffness.

Figure 23:
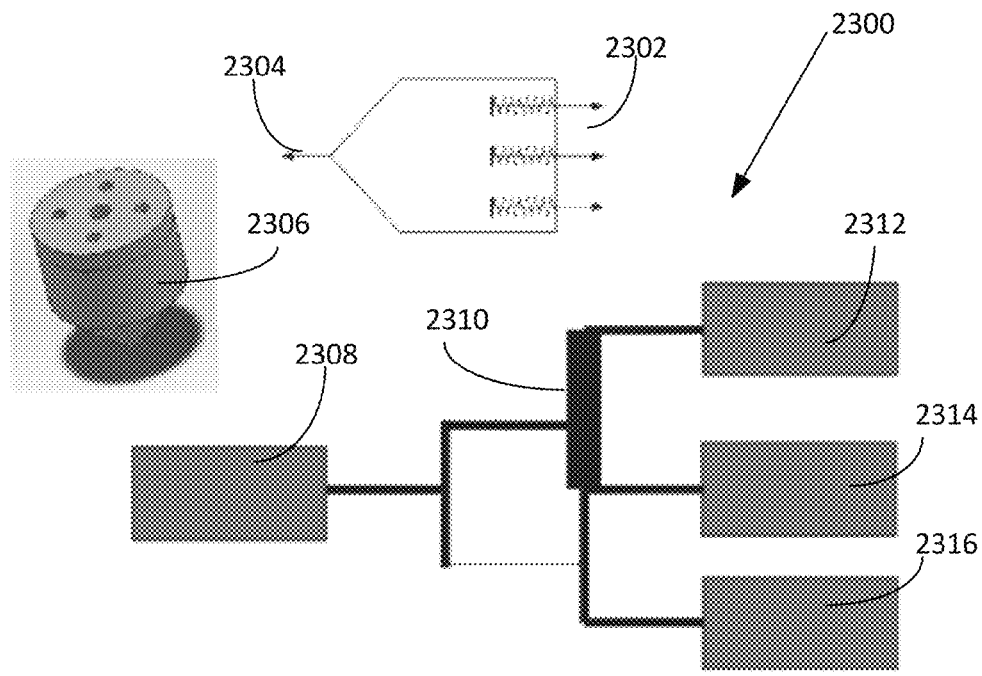
FIG. 23 is a schematic view illustrating one embodiment of a passive spring system for use in accordance with embodiments of the present invention.

FIG. 23 illustrates a further embodiment 2300 comprising a passive spring system 2302. System 2302 may be used for a variety of applications, such as in place of artificial tendons. 2306 is a housing for the spring system 2302. A rubber matrix 2310 connects the input force 2308 to output tendons 2312, 2314, and 2316.

Figure 24:
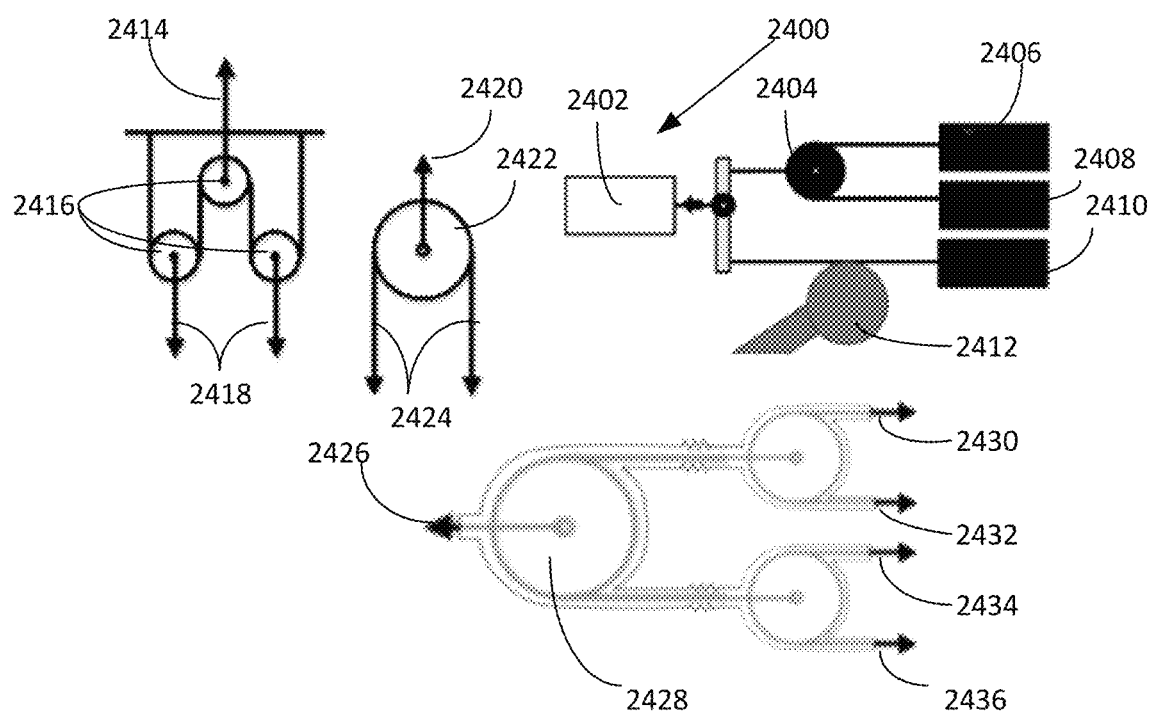
FIG. 24 is a schematic view illustrating multiple embodiments of loose pulley systems for use in accordance with embodiments of the present invention.

FIG. 24 illustrates several embodiments comprising pulley 2422 or hierarchical pulley 2416 and 2428 systems. System 2428 is enclosed within a sheath. System 2402 illustrates an embodiment comprising a pulley 2404, and a tensioner 2412 used to control the differential force between the input force 2402 and the output tendons 2406, 2408, and 2410.

Figure 25:
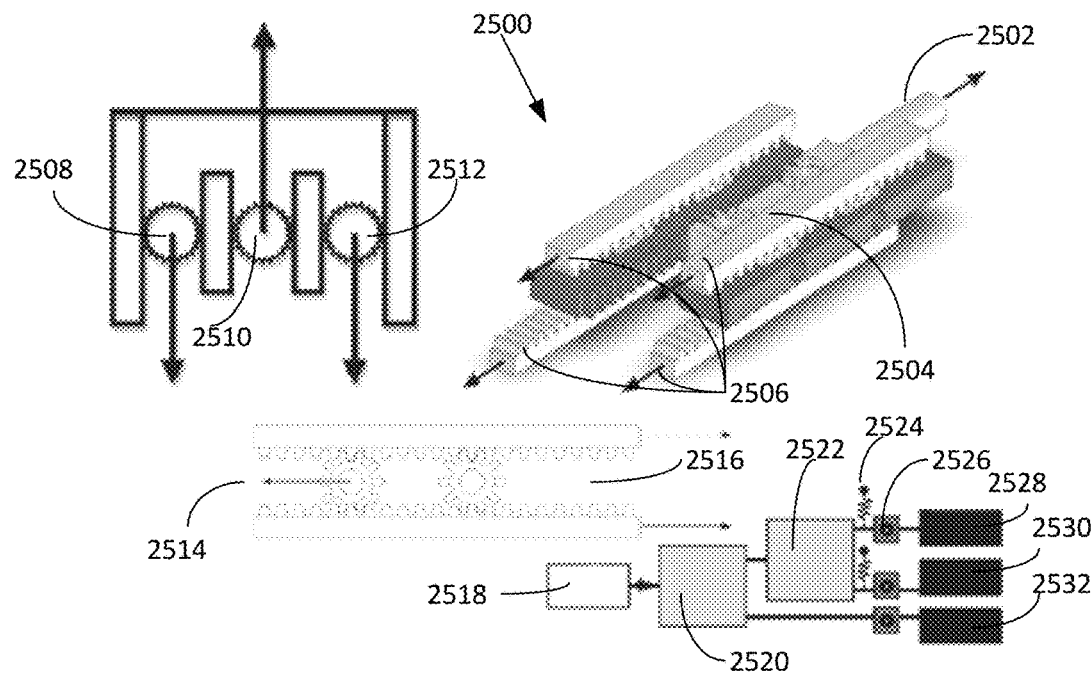
FIG. 25 is a schematic view illustrating planetary gear systems for use in accordance with embodiments of the present invention.

FIG. 25 illustrates an embodiment comprising planetary gears, 2500. Shaft 2502 comprises two or more gears 2504, which actuate movement of members 2506. Shaft 2502 is coupled to an input, such as a muscle, and members 2506 are coupled to output tendons. A further embodiment illustrates that gears 2508 and 2512 may connect to output tendons and gear 2510 may connect to an input muscle. A further embodiment illustrates that the planetary gear system may also be assembled hierarchically comprising an input muscle 2518 connected to a first set of gears 2520 having two ends. A first end connects through a gear ratio adjustment 2526 to an output and a second end connects to a secondary set of gears 2522, having two ends, each of which passes through a priority spring 2524 and connects to a gear ratio adjustment 2526 and then to an output 2528 and 2530. Planetary gears allow the subject to scale the amount of force transferred from the inputs to the outputs.

Figure 26:
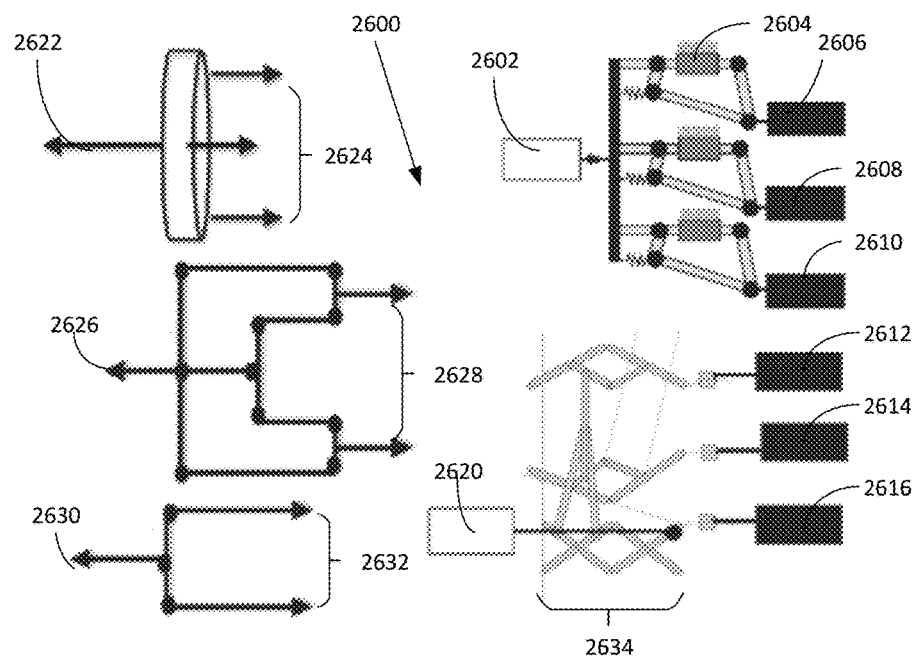
FIG. 26 is a schematic view illustrating multiple embodiments of linkage systems for use in accordance with embodiments of the present invention.

FIG. 26 illustrates several embodiments comprising variations on a linkage system 2600. In one embodiment, the input 2602 is connected to a series of slider joints 2604, which are in turn connected to each output tendon 2606, 2608, and 2610. In an alternate embodiment, a scissor lift linkage system can be used, wherein the input 2620 is attached to a system of connected scissor lifts 2634, which are connected to output tendons 2612, 2614, and 2616. In some further embodiments a rigid system comprises a connection to an input on a first end 2622, 2626, and 2630 and to output tendons 2624, 2628, and 2632 on a second end. In some embodiments for use in restoring the function of the hand, the linkage system allows the subject to vary the force generated at different points of the movement of the tendon, for example creating larger forces when the finger is flexed and smaller forces when the finger is open.

Figure 27:
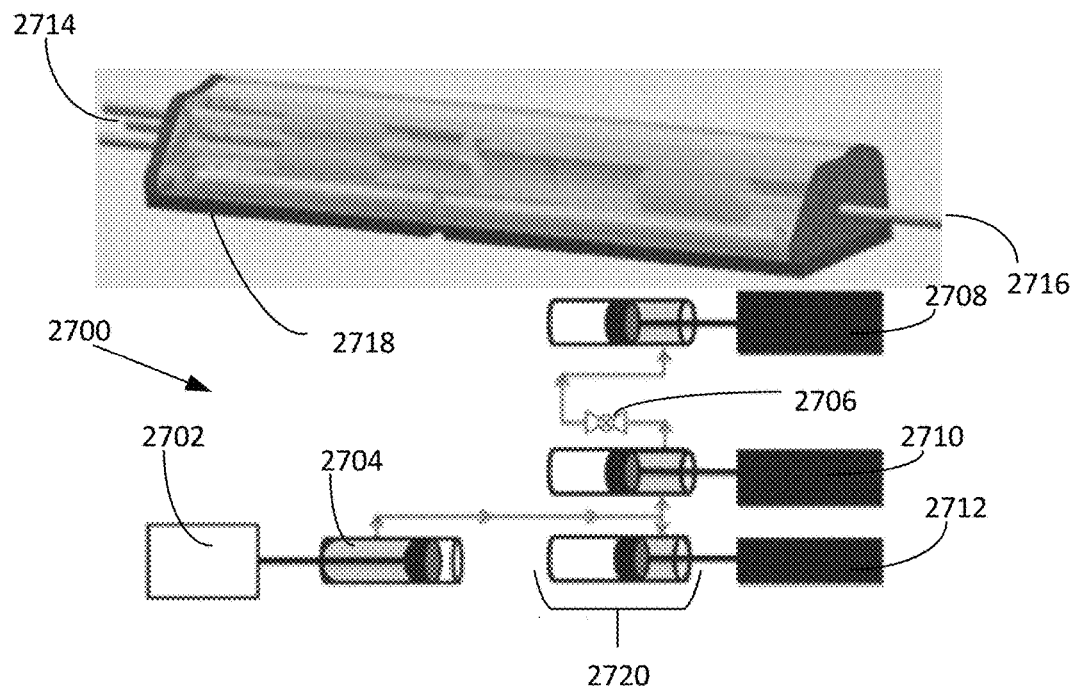
FIG. 27 is a schematic view illustrating one embodiment of a rigid hydraulic system for use in accordance with embodiments of the present invention.

FIG. 27 illustrates an embodiment comprising a rigid hydraulics system 2700. System 2700 connects an input force 2716, such as muscle to an output, such as tendons 2714. The schematic view illustrates that an input 2702 actuates hydraulic cylinder 2704, which actuates a second set of hydraulic cylinders, which are limited by a flow control valve, 2706. The cylinders then connect to the outputs, 2708, 2710, and 2712.

Figure 28:
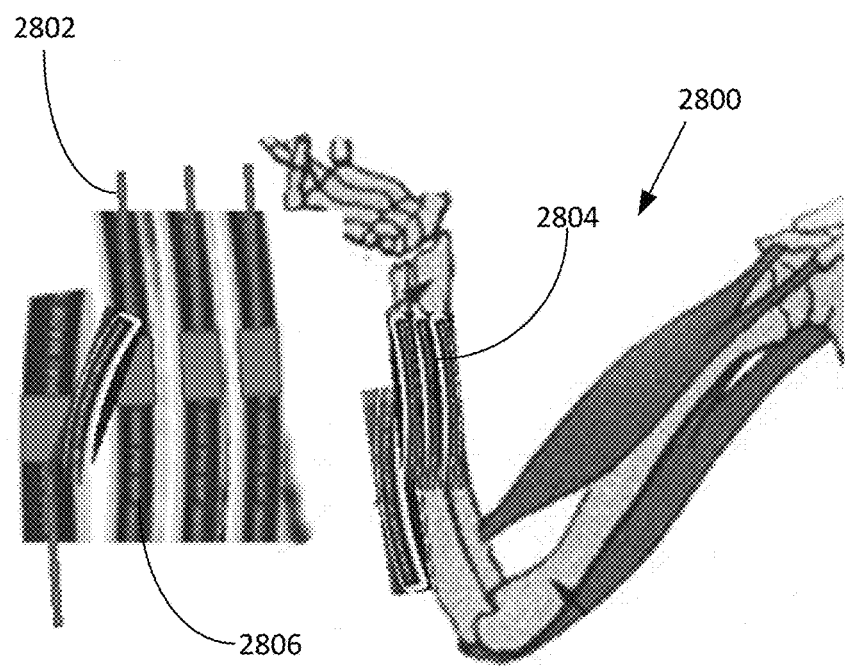
FIG. 28 is a side view illustrating one embodiment of a soft hydraulic system for use in accordance with embodiments of the present invention.

FIG. 28 illustrates an embodiment wherein the implantable mechanism is a soft hydraulic system, 2804. System 2804 connects the input, 2806, to the outputs, 2802.

Figure 29:
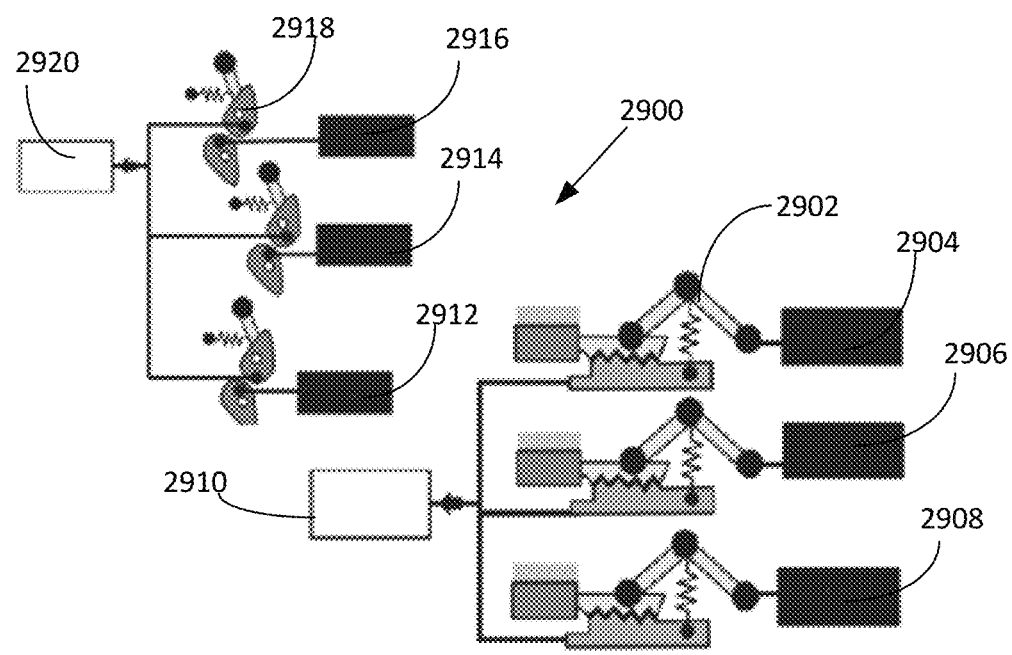
FIG. 29 is a schematic view illustrating one embodiment of a cam and clutch system for use in accordance with embodiments of the present invention.

FIG. 29 illustrates an embodiment wherein cam/clutch systems are used for connecting an input, 2910 or 2920, to outputs, 2904, 2906, 2908, 2912, 2914, and 2916, using cam/clutch systems 2902 and 2918. In some particular embodiments wherein the cam mechanism is implanted in a human hand, the subject can control the force to each finger depending on its posture. The radius of the cam determines how much force is transferred. In some embodiments wherein a clutch mechanism is implanted in a human hand, the clutch mechanism allows the subject to hold the output force in a certain location until the input muscle pulls, which breaks the clutch and restores movement.

Figure 30:
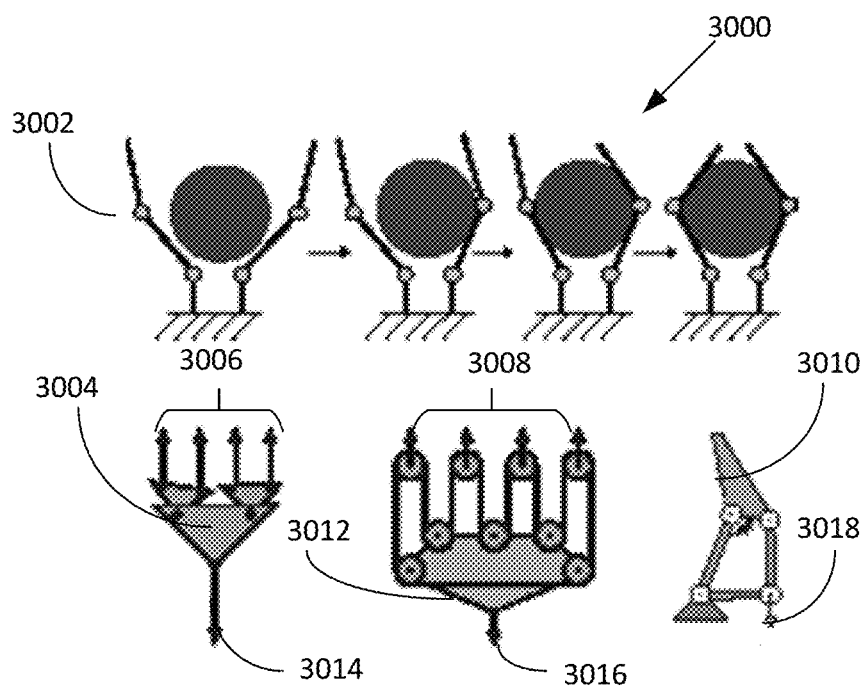
FIG. 30 is a schematic plan view illustrating several embodiments of implantable passive engineering mechanisms for use in accordance with embodiments of the present invention.

FIG. 30 illustrates several embodiments of passive engineered mechanism. An altered hierarchical triangle system wherein the input 3014 is connected to four output tendons, 3006, which pass through the triangle system, 3004. Another embodiment is the multiple pulley system, 3012, which allows the input 3016 to connect to four output tendons, 3008, which pass through a system of pulleys that are attached to a solid structure. Another embodiment is an anchored mechanism, 3010.

IV. Implantable Materials

A. Materials

In considering materials for implantable mechanisms biocompatibility, tensile strength, ability to remain inert, and resistance to fibrosis are useful characteristics to consider. Materials should not trigger inflammation or immune responses. Materials may be chosen based on one or all of the above considerations depending on what function they are serving.

Polymers are large molecules comprised of smaller related subunits. Polymer architecture, chain length, and arrangement affect the properties of the polymer. Longer chain lengths increase impact resistance and strength. Tensile strength of polymers increases as polymer chain length and crosslinking increase. With respect to polymers, suitable candidates include polyalkylenes, such as polytheylene, particularly Ultra High Molecular Weight Polyethylene (UHMWPE), nylon, polyester/polyethylene terephthalate (PET) and elastomers. Particular examples include polyparaphenylene terephthalate and combinations thereof.

In some embodiments, the materials implanted in the body will be metals and alloys. Metals and metal alloys may be chosen based on some, all, or none of the above considerations. Likely candidates for metals and metal alloys include titanium, stainless steel (only for temporary implants, least corrosion resistant), tantalum, and combinations thereof.

B. Coatings/Sheaths

In some embodiments the implantable materials must be coated partially or substantially completely to facilitate biocompatibility. Materials may be selected to inhibit or reduce fibrosis and tissue ingrowth and to inhibit biological adsorption and interaction events. Particular examples include but are not limited to polyurethane, phosphorylcholine, bovine submaxillary mucin coatings, covalently grafted non-fouling layers, surface immobilized brushes of chemicals including, but not limited to, sulfobetaine, and combinations thereof. In some embodiments component surfaces may be modified with a covalently-grafted, non-fouling layer or with a surface-immobilized brush (short polymeric chains densely grafted to a surface) of chemicals including but not limited to sulfobetaine (SB).

Accordingly, an exemplary list of suitable materials includes, but is not limited to, Ceramic materials, such as magnesium aluminate spinel (inert biocompatible ceramic); polymers, such as PEEK (polyetheretherketone), PEKK (poly(oxy-p-phenyleneisophthaloyl-phylene/oxy-p-phenyleneterephthaloyl-p-phenylene), carbon-reinforced polymer composites, polyester, PET, silicone, PTFE (polytetrafluoroethylene) or ePTFE (expanded PTFE), PUR (polyurethane), PFA (perfluoroalkoxy alkane), FEP (Fluorinated ethylene propylene), UHMWPE, polyesters, polyanhydrides, polyethylenes, polyorthoesters, polyphosphazenes, polyurethane, polycarbonate urethane, silicones, polyolefins, polyamides, polycaprolactams, polyimides, polyvinyl alcohols, acrylic polymers and copolymers, polyethers, cellulosics and any of their combinations in blends or as copolymers; silicone backbone-modified polycarbonate urethane; metals, such as titanium and tantalum; alloys, such as nickel titanium, cobalt chrome alloys, stainless steel, shape memory alloys, nickel cobalt, titanium niobium; minerals, such as tricalcium phosphate (TCP) (controls tissue response), pyrolitic carbon; and coatings, such as hydroxyapatite (HA) and PEG (polyethylene glycol).

In some embodiments the implantable materials may be fully enclosed in a biocompatible sheath to prevent interference with the surrounding biological tissues.

V. Implanting Methods and Method for Making

A. Implanting Methods

The implantable passive engineered mechanisms may be implanted and secured by existing surgical means, including but not limited to sutures, bone screws, bone anchors, or weaving.

Figure 44:
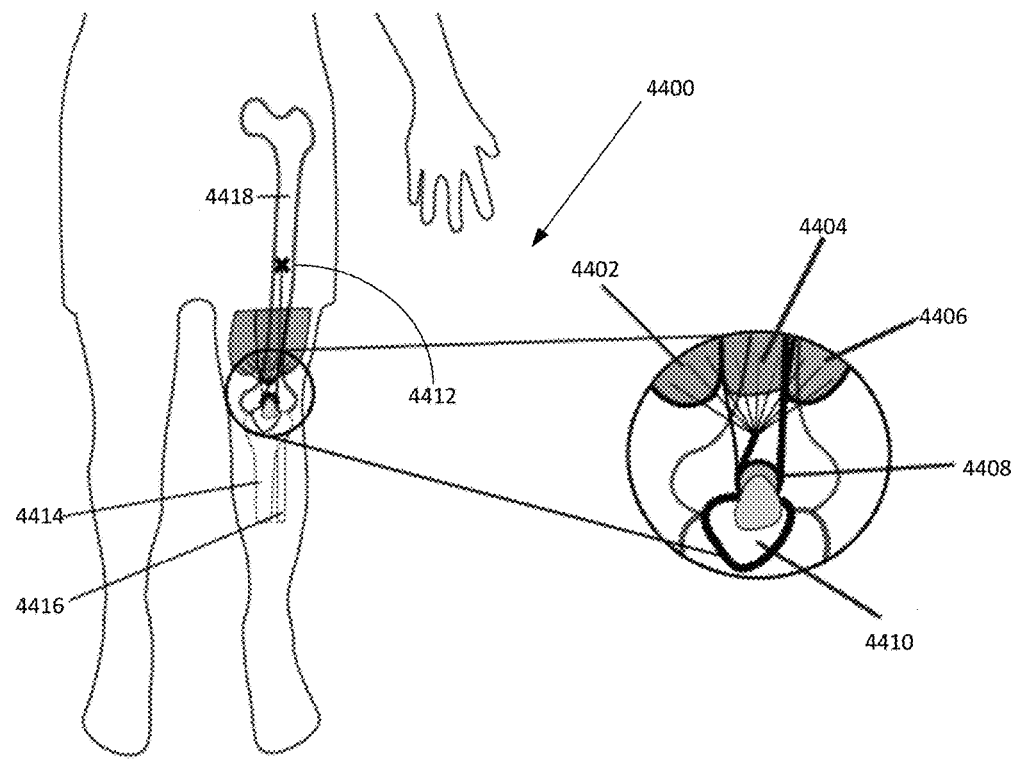
FIG. 44 is a schematic edge view illustrating one embodiment of a pulley mechanism implanted in a human knee joint.

As shown in FIG. 44, certain embodiments of the implantable passive engineered mechanism may be implanted in a knee joint. Where the mechanism is a pulley, 4408, the center of the pulley will be anchored using bone screws to the patella 4410. The pulley cable in the pulley will be anchored on one end to the femur (4418) and on the other end to the vastus medialis (4402), vastus intermedius (4404) and vastus lateralis (4406) muscles. In other embodiments the mechanism may be a lever, a triangular insert, a strut, a compliant mechanism, or a scissor lift.

Figure 45:
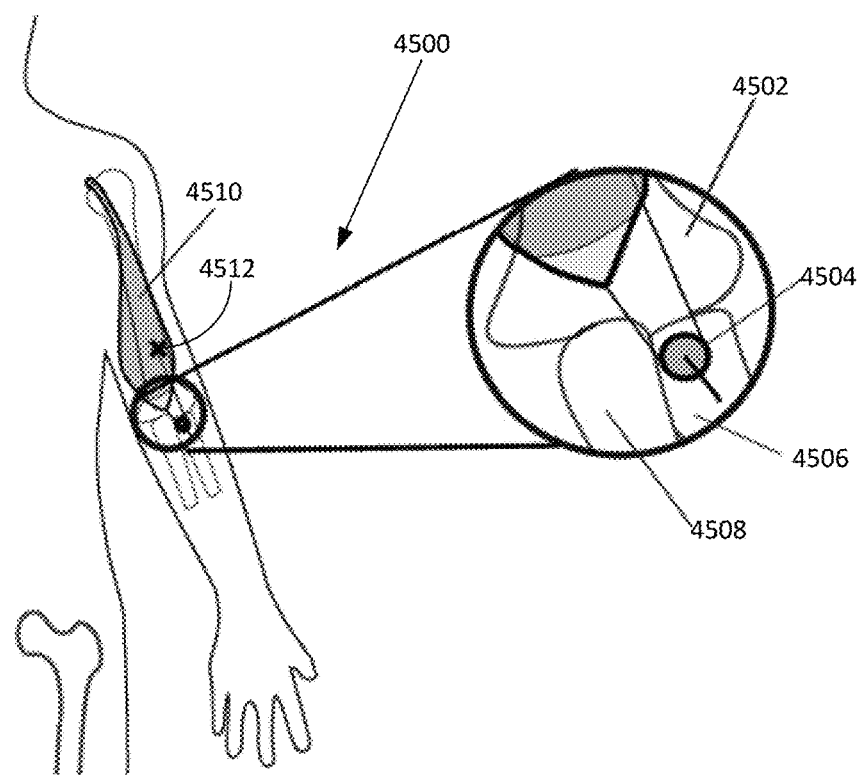
FIG. 45 is a schematic edge view illustrating one embodiment of a pulley mechanism implanted in a human elbow.

As shown in FIG. 45, certain embodiments of the implantable passive engineered mechanism will be implanted in an elbow joint. In some embodiments wherein the mechanism is a pulley, 4504, one end of the pulley cable surrounding will be effectively coupled to the end of the biceps brachii (4510). The other end of pulley 4504 will be anchored to the humurus 4512. The pulley 4504 itself is either anchored to the radius, 4506, or to a tendon of the forearm. In other embodiments the mechanism may be a lever, a triangular insert, a strut, a compliant mechanism, or a scissor lift.

Figure 46:
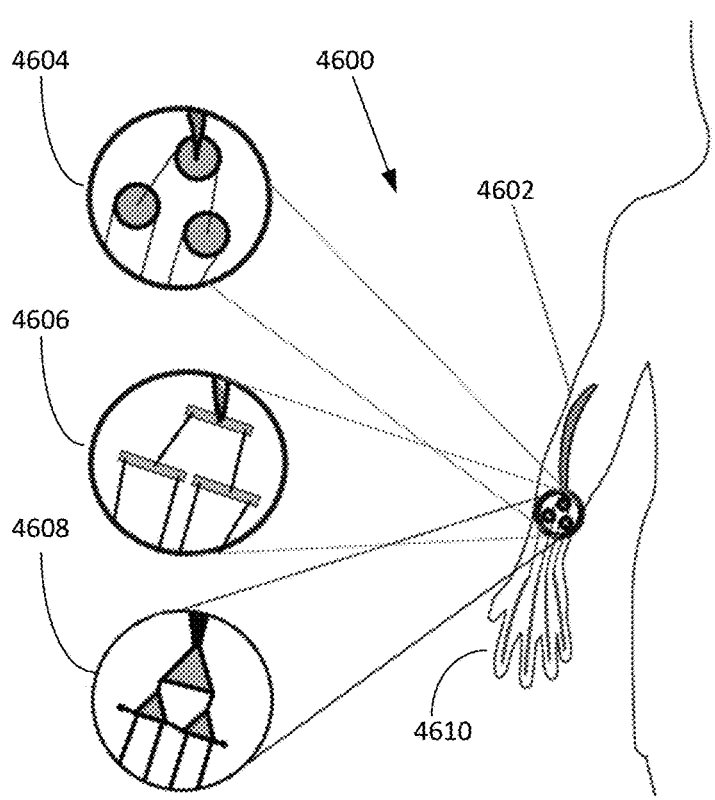
FIG. 46 is a schematic edge view illustrating one embodiment of a hierarchical pulley system, one embodiment of a hierarchical lever system, and one embodiment of a hierarchical tendon network implanted in a human arm.

As shown in FIG. 46, in certain embodiments the implantable passive engineered mechanism 4600 will be implanted in a human arm. For these embodiments the artificial tendon at the proximal end of the mechanism will be sutured to the ECRL muscle 4602 of the forearm. The artificial tendons at the distal end of mechanism 4600 will be sutured to the FDP tendons 4610 of the hand. Embodiments such as the hierarchical pulley system, 4604, the hierarchical lever system, 4606, and the hierarchical tendon network, 4608, may be implanted in this manner. Embodiments such as planetary gears, linkage systems, rigid and soft hydraulics, and cam/clutch systems also may be implanted in this manner.

In particular embodiments of the strut or insert mechanism, the input muscle may be sutured to two output tendons. The strut or insert will be positioned between and sutured to the output tendons. In embodiments implanted in the hand the ECRL muscle would be sutured to two of the FDP tendons, which would have the strut or insert positioned between and sutured to the FDP tendons.

In some embodiments, wherein the mechanism is a tendon network implanted in the arm, the distal ends of the tendon network are anchored to the radius and the ulna using bone screws. The biological FDP tendons are then sutured to the artificial tendons at the distal end of the network and the ECRL muscle is sutured to the artificial tendons at the proximal end of the network.

In particular embodiments of the soft parallel tendon mechanism or a passive spring mechanism, the mechanism is sutured on the proximal ends to the input muscle, and on the distal ends to the output tendons.

B. Making Disclosed Embodiments

In some embodiments, the implantable passive engineered mechanisms may be made using any method now known or hereafter developed as will be understood by a person of ordinary skill in the art by methods including, but not limited to, 3D printing, Computer Numerical Control (CNC) Milling and/or Shape Deposition Manufacturing (SDM).

VI. Examples

The following examples are provided to illustrate certain particular features and/or embodiments. These examples should not be construed to limit the disclosure to the particular features or embodiments described.

Example 1

Figure 31:
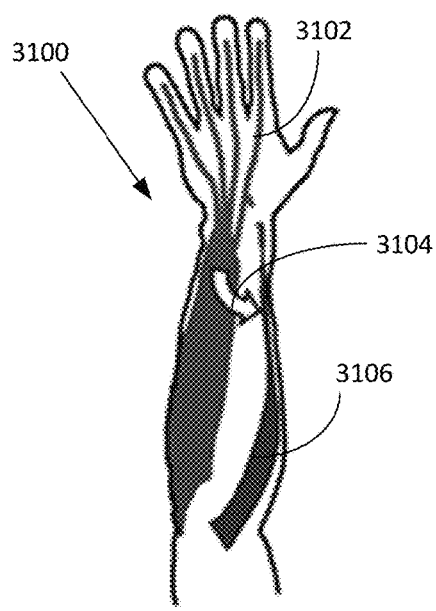
FIG. 31 illustrates the major tendons and muscles in the human arm.

This example demonstrates the differences in grasping ability between the current suture based tendon-transfer procedure for high-median ulnar palsy and the tendon-transfer procedures using implanted pulley and lever based passive mechanisms. FIG. 31 illustrates the current high-median ulnar palsy tendon-transfer procedure, wherein the FDP tendons (3102) are sutured to the ECRL (3106).

Figure 32:
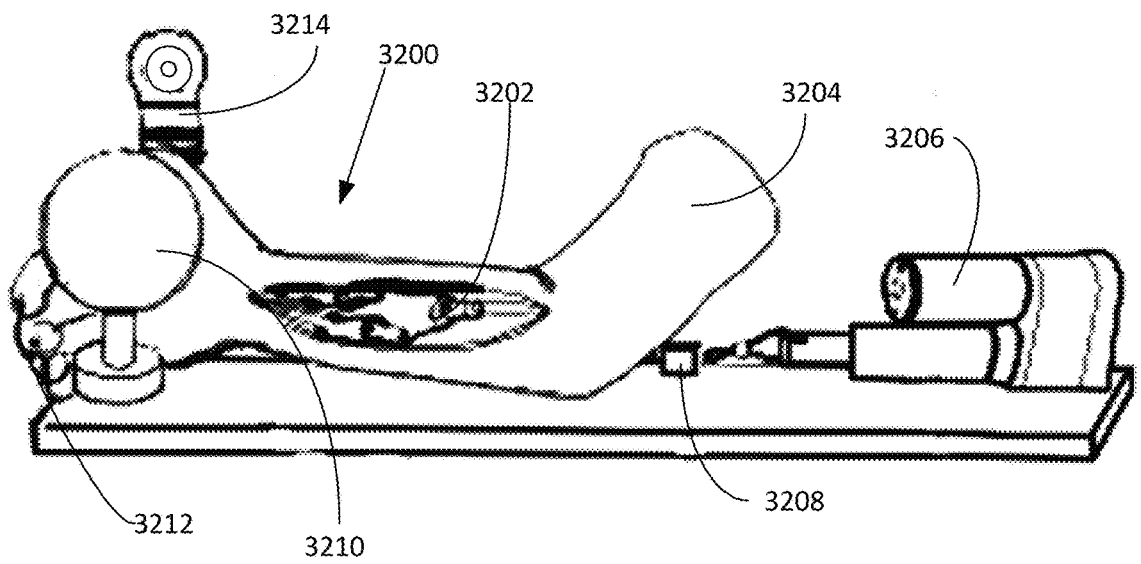
FIG. 32 is a schematic edge view illustrating an experimental set-up for testing the grasping ability of cadavers having an implanted hierarchical pulley system.

Both the suture-based procedure and the implanted pulley-based tendon transfer procedures were conducted on six cadaver arms with mean age of 90.6±2 years. The cadavers were thawed for a minimum of 24 hours and had reached a steady-state temperature before the first procedure was conducted. FIG. 32 illustrates the experimental set-up. The cadaver arm, 3204, was secured with bone screws to a horizontal test rig with the ulnar side along the table surface. The fingers were set in their rest position. A 3.5-cm-diameter rigid sphere on top of a 2.5-cm-height rigid stem, 3210, was attached to the table surface in front of the palm for grasping. Finger movement was created using a linear servomechanism (positioning motor) coupled to the ECRL tendon 3206. A single-axis load cell measured the actuation force applied. For each arm, the suture-based procedure was performed first and the grasping task was conducted. Then, the pulley-based procedure, 3202, was performed and the grasping task again performed. Reflective markers were placed along the hand 3212, to track finger movement using a five-camera Optitrack motion-capture system 3214 operating at 30 Hz.

Figure 33:
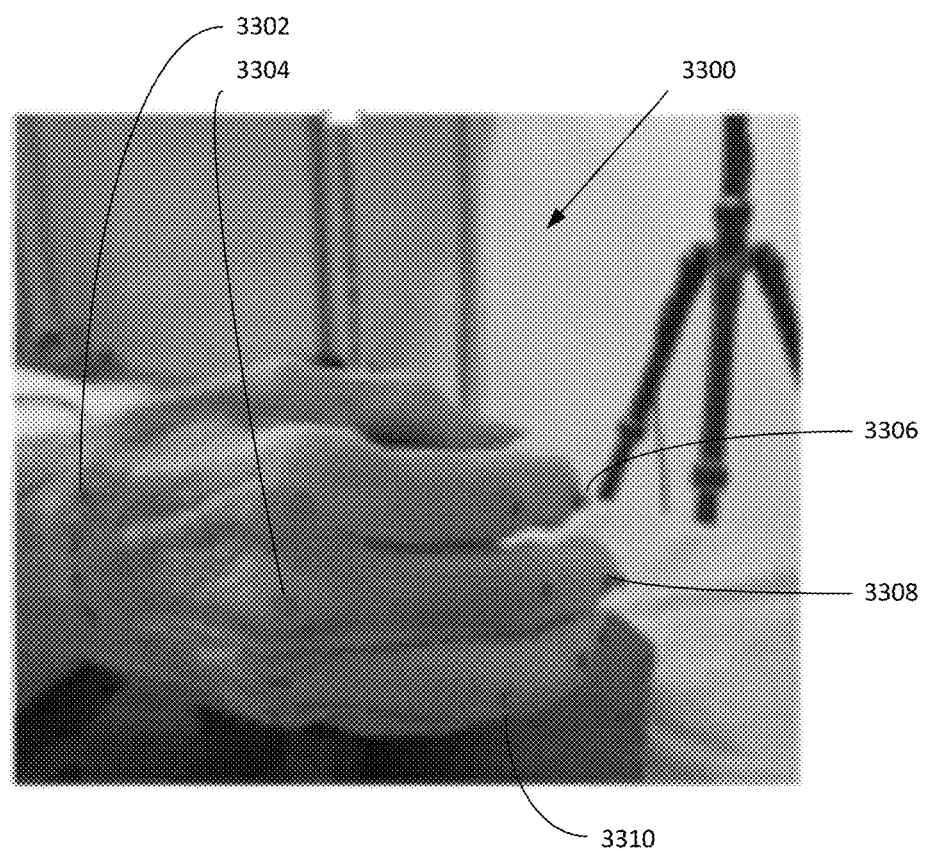
FIG. 33 is a photograph of a cadaver hand with reflective markers placed at the joints to allow capture by a camera system.

FIG. 33 shows that the four-millimeter reflective markers were placed on the finger tips, 3308, distal interphalangeal (DIP) joints, 3306, proximal interphalangeal (PIP) joints, 3310, metacarpal phalangeal (MCP) joints, 3304, and carpometacarpal (CMC) joints, 3302. A separate video camera was also used to record each trial. After each trial, the servomechanism was reset while keeping the ECRL tendon taut, and the fingers were manually returned to the rest position. An average of 5±2 trials were conducted for each cadaver-procedure pair.

In the suture-based procedure, the ECRL tendon was routed in between the ulna and radial bones and directly sutured to the four FDP tendons with an "end-to-side" technique. The ECRL tendon was cut from the muscle belly and attached to the linear servomechanism to produce tendon excursion.

In the pulley-based procedure, the ECRL tendon was sutured to a cable attached to a proximal pulley. The ring and small finger FDP tendons were sutured to a cable wrapped around a distal pulley, while the index and long finger tendons were sutured to a cable wrapped around a second distal pulley. The heads of both distal pulleys were attached with a cable that was wrapped around the proximal pulley. The proximal pulley had a diameter of 20 mm and was 10 mm thick, weighing 4.6 g. The distal pulleys were 15 mm in diameter and 10 mm thick, weighing 3.7 g. The cables were made of pre-strained 0.86-mm nylon-coated stainless steel. The forearms were sewn closed after the pulley mechanism was in place.

Synchronized data streams from the single-axis load cell, motion capture system, and linear servomechanism were collected using National Instruments Labview software. The experimenter commanded the servomechanism's excursion in steps of 1.8 mm. The total servomechanism travel never surpassed the ECRL's optimal fiber excursion length of 8.1 cm. The servomechanism actuation was continued until all the fingers made contact with the ball or a maximum of 150 N in actuation force was reached. The actuation force used was thus less than the ECRL's maximum force of 304 N.

A. Analysis—Actuation force

To analyze the force required by the ECRL to grasp the sphere, the actuation force applied by the servomechanism was recorded at the point where all fingers made contact with the ball for each trial by the single-axis load cell. The actuator force measured for each procedure and subject were averaged across the trials, such that Fsi represented the mean actuator force for subject i for the suture-based procedure, and Fpi the mean actuator force for the subject i for the pulley-based procedure. In order to test if the pulley-based procedure enabled grasp creation at lower actuation forces statistical significance of the force data for each subject was tested with a one-sided paired t test between the procedures.

In addition, the ratio $R_{fi}=(F_{pi}/F_{xi})$ of the mean actuation forces between the two procedures was also computed for each subject i. The ratio of forces $R_{fi}$ was averaged across all subjects to compute $R_F$.

B. Analysis-Finger Movement During Grasping

The finger movement during a trial was processed using the OptiTrack Motive motion capture software to create time history data of each of the joint angles for each finger. Each finger's movement during the grasping process was quantified as the sum of movement of all the joints ($\Sigma\theta i=\theta MCP+\theta PIP+\theta DIP$). The digital videos were analyzed to visually determine the time that each finger contacted the ball, which defined the stages of the grasping process.

This experiment quantifies the adaptability in finger movement during grasping as the relative movement of fingers that have contacted the object with respect to the movement of fingers that have not contacted the object. The goal was to show the improvement in grasping capability through the entire grasping process and not just the final grasping state. This is because the grasping process involves a staggered interaction between the fingers and the object and the grasp can fail at any point. With this goal, the grasping process during each trial was split into four phases based on the sequence of fingers making contact: phase 1, movement beginning to first finger contact; phase 2, period between first finger contact and second finger contact; phase 3, period between second contact and third contact; and phase 4, period between third finger contact and fourth finger contact (full contact).

Figure 34:
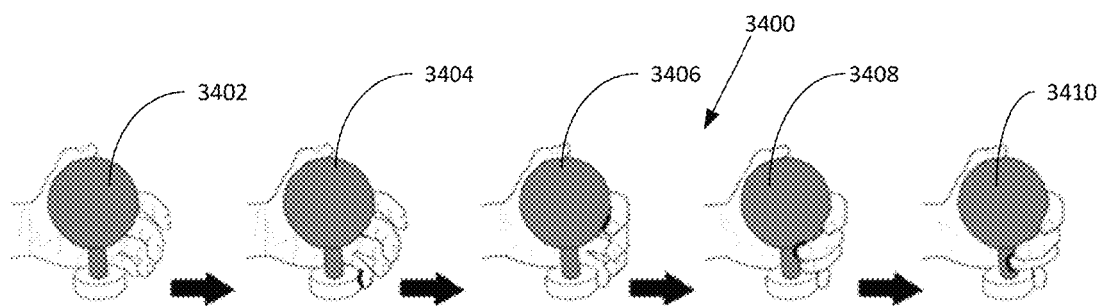
FIG. 34 is a schematic edge view illustrating the phases of finger contact during the grasping process of a hand with an implanted hierarchical pulley system.

FIG. 34 illustrates each phase of the grasping process for subject 6. 3402 shows the initial movement, 3404 first finger contact, 3406 second finger contact, 3408 third finger contact and 3410 fourth finger contact/full contact. Note that in some trials, some fingers made contact with the object at the same time. Such trials would have fewer grasping phases.

For each of the grasping phases, the summation of the change in joint angles, $\Sigma\Delta\theta_c$, for the fingers that established contact and the fingers that had not established contact, $\Sigma\Delta\theta_{nc}$, was computed for each phase. It was expected that (1) the sum of the change in joint angles after contact, $\Sigma\Delta\theta_c$, would be lower for the pulley-based procedure when compared with the suture-based procedure, and (2) the sum of the change in joint angles after contact $\Sigma\Delta\theta_c$ would be less than the sum of the change in joint angles $\Sigma\Delta\theta_{nc}$ for the pulley based procedure. This would indicate two things: (1) less slip of the fingers on the object during the grasping process; and (2) better adaptability of the fingers to the objects shape during the grasping process. For the suture-based procedure, $\Sigma\Delta\theta_c$ is expected to be equal to $\Sigma\Delta\theta_{nc}$, showing coupled finger movement through the grasping process. The movement of the fingers that have not yet contacted the ball $\Sigma\Delta\theta_{nc}$ was also compared for the suture-based procedure and pulley-based procedures in order to verify if the pulleys hindered finger movement. Statistical significance was determined with an independent sample t test based on the mean of the joint angle changes computed across all the trials and subjects.

C. Results

Figure 35:
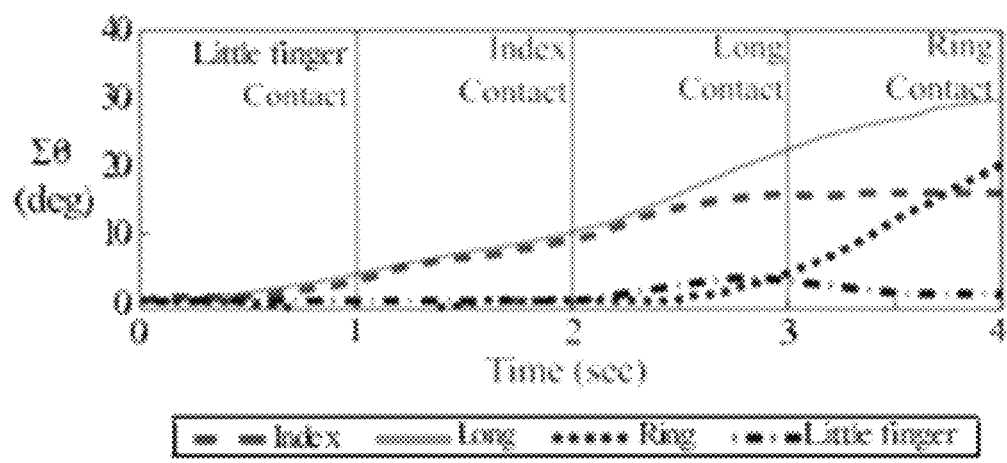
FIG. 35 is a graphical representation of the angle of finger contact as a function of applied force over time.
Figure 36:
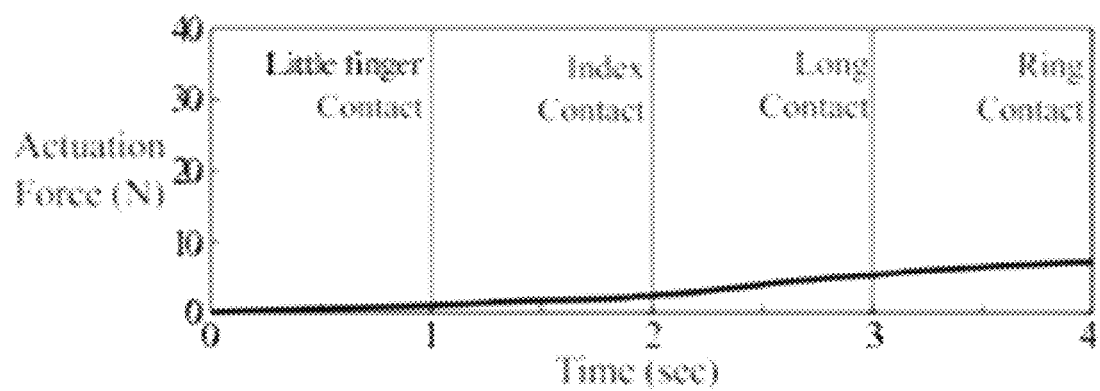
FIG. 36 is a graph of time versus actuation force illustrating the actuation force of each finger over time.

A total of 29 trials for the suture-based procedure and 32 trials for the pulley-based procedure were analyzed across all of the subjects. Trials were omitted if the motion capture data could not be trajectorized due to marker occlusion or the markers could not be individually distinguished. This is because the markers placed on the fingers can come very close to each other during the grasping process. Also, the force required to create a full grasp is much greater for the suture based procedure than the pulley based procedure. FIG. 35 illustrates the joint angle over time for each finger. FIG. 36 illustrates the actuation force required for establishing full contact between the fingers and the object over time.

Figure 37:
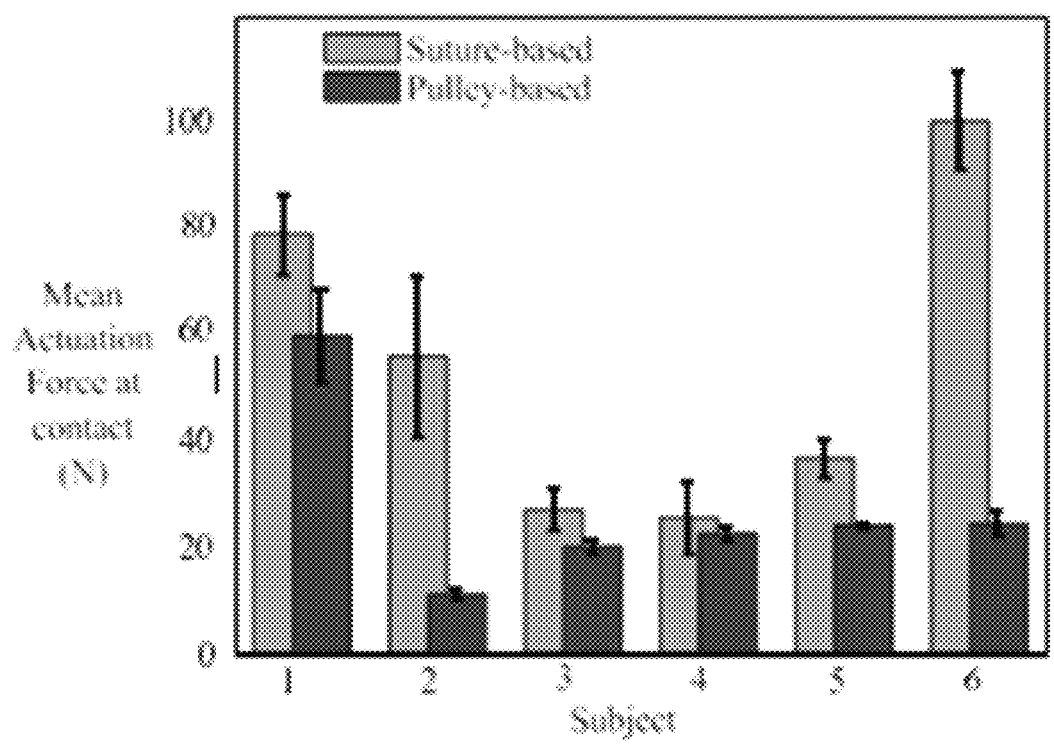
FIG. 37 is a graph of subject versus mean actuation force comparing the mean actuation force at contact for subjects having suture-based and pulley-based procedures.

FIG. 37 illustrates the mean actuation force required for establishing full contact between the fingers and the object for the pulley based and the suture based procedures. A paired t test across all subjects showed that the mean actuation force required following the pulley-based procedure was significantly lower than the force required for the suture based procedure (p value 0.03). Furthermore, the mean of the ratio of forces across the subjects was RF=0.55±0.12, indicating that the pulley-based procedure decreased force requirement by 45% on average across the subjects. Note that the intersubject variability in actuation force is likely because of different innate properties of each cadaver such as tendon or joint stiffness, finger lengths, finger rest position, and slippage.

For the 32 trials for the pulley-based procedure, there were 73 phases during the grasping process between the time when finger(s) made contact on the object and the subsequent finger(s) made contact (compared to an expected 96 if all fingers touched at separate times). The 29 trials for the suture-based procedure had 55 phases during the grasping process (compared to 87 expected). The remaining phases could not be analyzed due to incomplete motion capture data.

For the pulley-based procedure, the mean joint angle change for fingers that made contact ($\Sigma\Delta\theta_c$=2.99°±0.28°) was significantly different (p value<0.001) from the mean joint angle change for fingers that did not make contact ($\Sigma\Delta\theta_{nc}$=6.42°±0.57°). The suture-based procedure mean joint angle changes, $\Sigma\Delta\theta_c$=6.22°±0.66° and $\Sigma\Delta\theta_{nc}$=6.14°±0.75°, were not significantly different from each other (p value 0.9). The mean values of $\Sigma\Delta\theta_c$ across all six subjects for the pulley-based procedure were significantly less in value<0.001) than the corresponding values for the suture-based procedure.

A key aspect of the grasping process is that it is difficult to predict which finger will make first contact with the object and where on the object it will make contact due to uncertainty in hand position or object shape. A healthy person overcomes this uncertainty through control over individual finger flexion. However, this is a significant issue for a patient with impairments, since the subject may not have individual control of finger flexion and proper tactile or proprioceptive feedback. Furthermore, the patient may be re-learning to use their musculature after a tendon transfer surgery. Specifically, patients who undergo the suture-based procedure for restoring finger flexion following high median ulnar palsy have coupled finger movement. Thus, the fingers do not adapt individually to the object's shape during grasping, forcing the patient to perform awkward wrist and arm movements to create a secure grasp. This effect will be most prominent when grasping objects of irregular shape.

The implanted pulleys in the new procedure address this problem by enabling the fingers to individually adapt to the object shape and close in on the object using 45% less actuation force than the force required following the suture-based procedure. The unused muscle force may be used to increase grip strength after the fingers close in on the object. For example, for the suture-based procedure, if the fingers make contact with the object in a staggered fashion (either due to the object shape or tendon tensioning error), then the muscle must stretch the tendons of the fingers that have already established contact with the object in order to close the fingers that have not yet made contact. This would require greater actuation force than normal finger flexion which would only work against the much lower joint stiffnesses. Two benefits of the reduced force requirement after the pulley-based procedure are that (1) it could increase the number of candidate donor muscles for the surgery, and (2) it would mitigate the effects of losing muscle strength that is typical in tendon transfer surgery.

The pulley-based procedure also leads to significantly better finger movement in terms of enabling the fingers to individually wrap around the object even when actuated by just one muscle. This is quantified through four major comparisons between the pulley-based and suture-based procedures based on the movement of fingers before and after making contact with the object. First, for the pulley-based procedure, the mean joint angle change $\Sigma\Delta\theta_c$ for those fingers that make contact is significantly smaller than the mean joint angle change $\Sigma\Delta\theta_{nc}$ for the fingers that have not contacted the object. This comparison shows that following the pulley-based procedure, the fingers that made contact move much less than the fingers that have not yet made contact and that the grasp changes minimally after each stage of the grasping process. Second, the mean joint angle change before and after contact for the suture-based procedure is similar, showing that the fingers have coupled movement even after contact has been made. This implies that the fingers that have made contact slip on the object's surface at the same rate that the fingers that have not made contact close in on the object.

Third, the mean joint angle change for those fingers that have made contact, $\Sigma\Delta\theta_c$, across all six subjects is significantly less for the pulley-based procedure when compared with the suture-based procedure. This indicates that the fingers that made contact after the pulley-based procedure do not slip as much on the object as the fingers after the suture-based procedure. Specifically, the suture-based procedure would lead to more than 18° joint angle change in the first finger to make contact at the end of a three-stage grasping process, 12° for the second finger to make contact, and 6° for the second finger that makes contact. This would result in a significant difference between the initial and final grasps. In contrast, the pulley-based procedure would only lead to half of the joint angle change between the initial and final grasps. Fourth, finger movement before making contact with the object was similar for both the pulley-based and suture-based procedures. This indicates that the pulleys do not hinder finger movement.

These promising results from cadaver studies establish that the pulley-based tendon transfer surgery improves hand function compared to the suture-based procedure. However, some challenges must be overcome before this procedure can be used clinically. First, in addition to fabricating the device using biocompatible materials such as titanium or ultra high molecular weight polyethylene (UHMWPE), the mechanism may have to be chemically coated to reduce fibrosis when implanted in vivo long-term. Second, the pulley-based procedure also depends on technology to make attachments between the biological tendon and the mechanism's artificial components. Third, the mechanism may have to be enclosed in a sheath of biocompatible material in order to reduce injury to surrounding tissue while the mechanism moves inside the forearm.

Example 2

This example demonstrates two embodiments of implantable passive engineered mechanisms for hand tendon-transfer surgery (1) a tendon network; and (2) a moving lever mechanism.

The tendon-network implant was added to the OpenSim upper-extremity model using a web of tendons similar in properties to biological tendon. The tendon network has an equilateral triangular structure in order to distribute the forces and movement from one input (a muscle) across two outputs equally. This equilateral triangle is 32 mm long on each side. The proximal end of the network is attached to the ECRL muscle while the distal ends are attached to the finger tendons. The artificial tendons are chosen to have the same stiffness properties similar to biological tendons (normalized resistance force $F=1.6x^2-1.4x-0.2$, where x is the tendon strain). The physical version of the tendon network will be constructed from Kevlar or polyvinylidene fluoride (PVDF), which have favorable biological compatibility and mechanical properties. Since the tendon network is not rigid, it is anchored to the forearm bones (the ulna and radius bones) in order to maintain structure. The three ends of the triangle are allowed to slide in a plane parallel to the bones and thus each have three degrees of freedom. The anchor points are anchored to bones. The same triangular structure can be hierarchically assembled to create differential action from one muscle across more than two tendons.

The moving-lever mechanism was added to the basic OpenSim upper-extremity model in the form of a single rigid cylindrical element (these models may be designed in 3D modeling software such as AutoCAD or created inside OpenSim itself). The ECRL muscle was connected at the center of the cylinder and the FDP tendons were attached at the two ends of the cylinder. Offsetting the position of the ECRL attachment to either side of the center would create larger forces on the tendon on that side, thus enabling scaled distribution of forces between the fingers. The cylinder was provided three degrees of freedom to translate and rotate in the plane. One challenge with the lever mechanism is that it would have to be long for large muscle contractions. This is because the lever mechanism ceases to create differential action when it rotates beyond 80 degrees. Specifically, calculations show that the tendon of one finger could travel up to 2.5 cm with a 3 cm long lever after another finger is stopped due to contact during grasping.

Since the ECRL's maximum excursion capability is 3.9 cm, the patient would have to sacrifice some finger flexion capability for having the ability to scale the force transferred to different fingers. Three models, a suture procedure model and the two implant models, were compared. In all three models, finger movement was created by setting the ECRL to have a linear-ramp-and-plateau activation profile (linear ramp over 3 seconds from 0 to 75% excitation, and then held at 75% for 3 seconds). Contact between the fingers and the target object during the grasping process was simulated by creating contact between the index fingertip and an external rigid constraint as soon as the index finger flexed. The fingertips were set to be stiff with static, dynamic, and viscous friction coefficients of 0.8, 0.75, and 0.01 in order to represent the physical interaction between the human fingertip and the objects for grasping. Finger movement was measured using the "total flexion" of all three flexion joints (MCP, PIP, and DIP) in the finger. The differential movement and fingertip force created by the muscle action across the index and middle fingers were measured in each simulation.

A. Results

Figure 38:
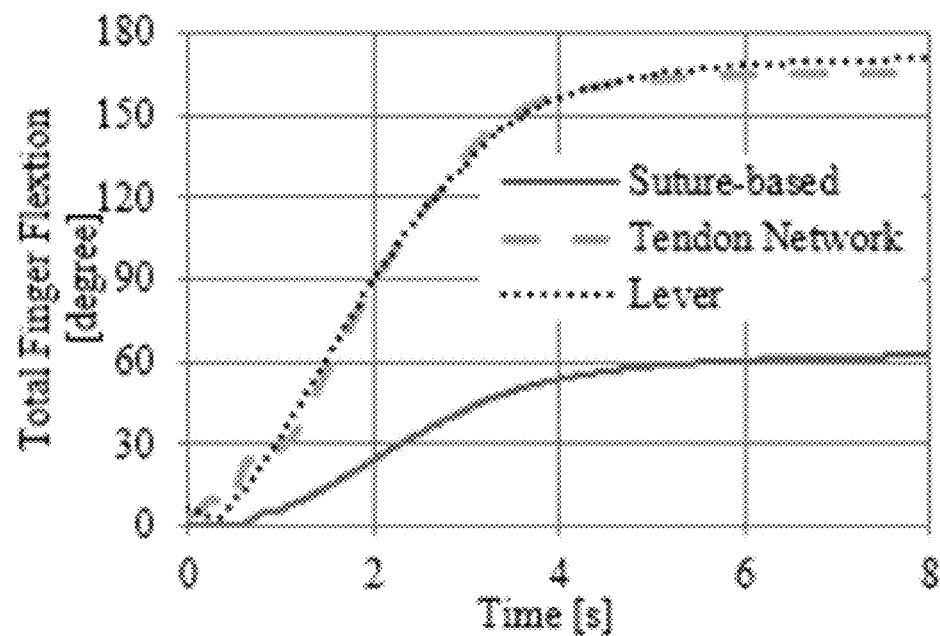
FIG. 38 is a graph of total finger flexion versus time comparing total finger flexion over time for suture-based, tendon network, and lever based procedures.

FIG. 38 illustrates the large difference in finger flexion enabled by the implanted tendon-network and moving-lever mechanisms when compared to the finger flexion enabled by the suture-based procedure when the fingers close in to grasp an object of uneven shape. Specifically, both the implanted tendon-network and moving-lever mechanisms provide nearly 170 degrees of differential movement between the index and middle fingers, which is nearly three times the differential movement (62 degrees) enabled by the suture-based procedure. It was confirmed that the ECRL force was equal in all three cases, 275 (N), confirming that the differential action was due to the implanted mechanism.

Conversely, it was also observed that less muscle force was required to close the fingers to the same extent following the implant-based procedure. Thus, when establishing a multi-finger power grasp, the fingers would adapt better to the object's shape at lower actuation force following the implant-based procedure.

While the above results show that the implant-based procedure improves finger adaptability during power grasps, the influence of the suture-based and implant-based procedures during index-thumb precision grasp was also analyzed. Specifically, the suture-based procedure enables the immediate creation of a precision grasp once the index finger makes contact with the object, since the movement of all the fingers ceases immediately after the index finger makes contact. Thus, the contact force established between the index finger and the object is expected to be large. In the case of the implant-based procedure, strong contact forces can be established only after the other fingers also close in. This marginally reduces the contact forces that may be established in the precision grasp following the implant-based surgery. However, the simulations showed that the fingertip force enabled by the implant-based procedure in pinch grasps is still comparable to the fingertip force of a healthy person (about 27.9 N). Thus, the implant-based procedure is able to create differential action between multiple fingers to improve power grasping capability, while also enabling sufficient strength in pinch grasps similar to that of a healthy individual.

Example 3

This example demonstrates an embodiment of an implanted passive engineered pulley-based mechanism that is used in knee-joint surgery.

In order to restore knee strength following knee-replacement surgery, a pulley mechanism could be implanted between the quadriceps and the patella. The pulley would scale the quadriceps force by about 200%, while sacrificing about 50% of the range of motion. Such partial loss of range of motion in the knee is acceptable, because only 105 degrees of movement is necessary for daily activities. The pulley was incorporated into the basic OpenSim lower-extremity model by inserting and attaching an additional tendon to the four quadriceps muscle heads, routing it through a via point on the patella, and then anchoring it to the femur bone. This routing acts as a pulley because the tendon is free to slide around the via point on the patella. In both models with and without the implant, knee joint movement was created by setting all four quadriceps muscles to have a linear-ramp-and-plateau activation profile (linear ramp over 3 seconds from 0 to 75% excitation, and then held at 75% for 3 seconds). The knee joint torque was estimated using the force in a virtual spring attached to the tibia. This spring was modeled in OpenSim using a tendon with the same force-length curve as biological tendons. The knee joint's initial position was 54 degrees, and the knee joint's change in angle was measured.

A. Results

Figure 39:
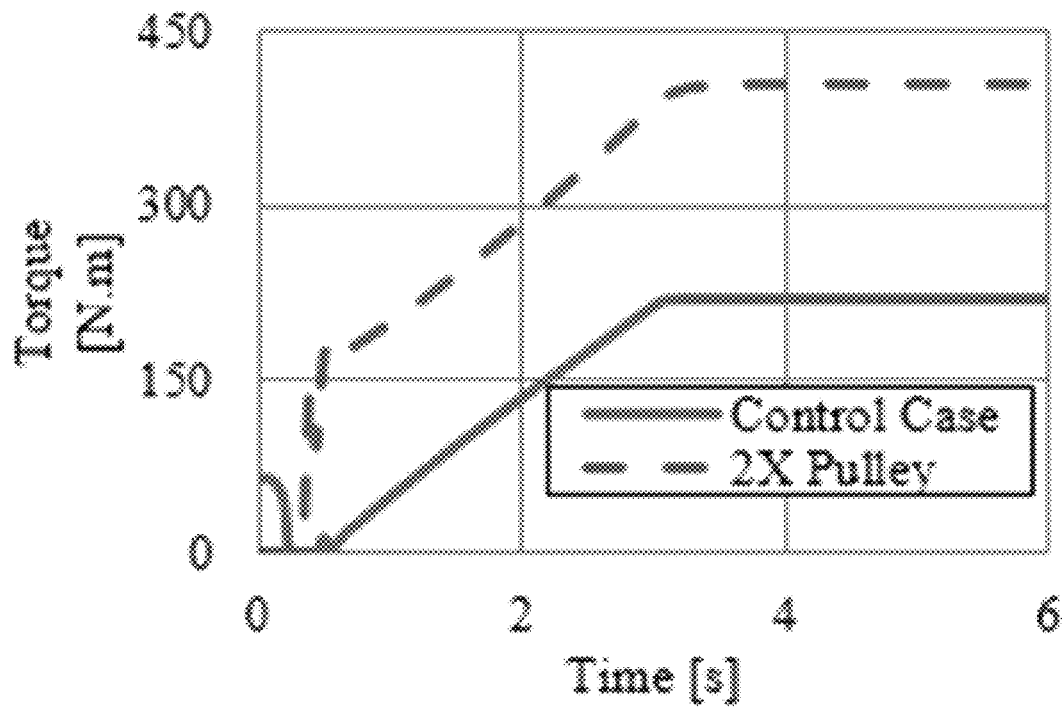
FIG. 39 is a graph of torque versus time knee joint torque between a control (suture-based) procedure and a 2× force multiplying implanted pulley.
Figure 40:
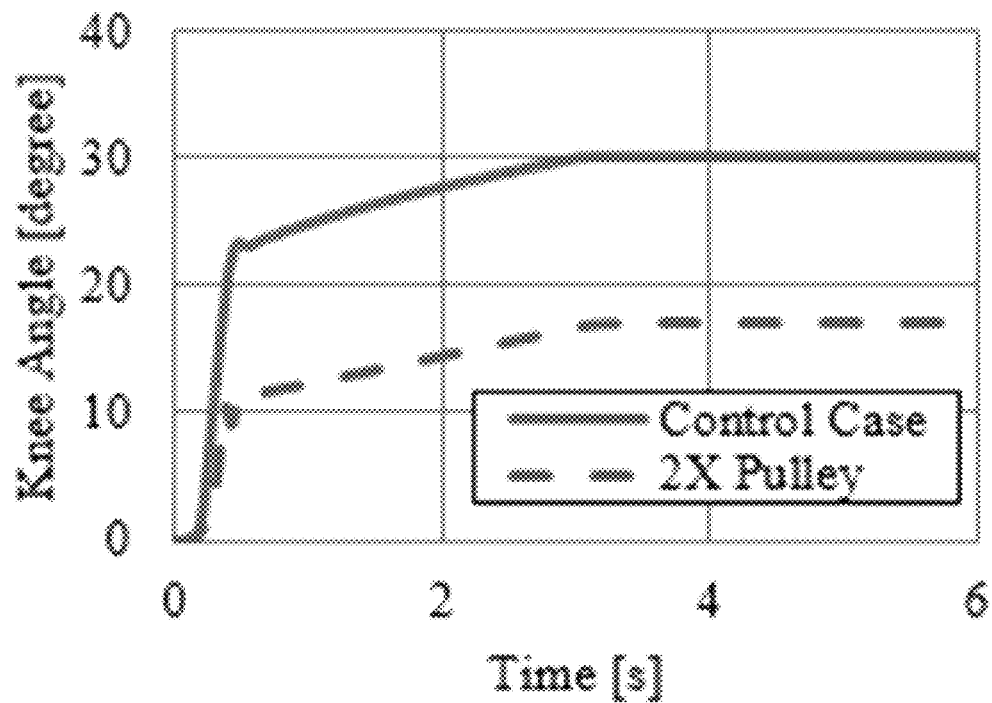
FIG. 40 is a graph of knee angle versus time comparing knee angle between a control (suture-based) procedure and a 2× force multiplying implanted pulley.

FIGS. 39 and 40 illustrate the time-history of the knee-joint torque and the knee-joint angle change due to quadriceps activation following the standard surgery and following the implant-based surgery. The knee joint torque generated following the implant-based surgery is 1.84× the force generated in the suture-based procedure. A force scaling of 2× was expected, but the reduced scaling arises from the irregular lines of action for muscles and ligaments in the human body when compared to mechanical systems. Specifically, if the directions of the input and output tendons are not perfectly aligned or in the plane, the angular discrepancy will affect the magnitude of force scaling. The range of motion correspondingly decreased 0.56× when using the implant.

The uniqueness of the proposed work is that the passive implants better utilize the patient's own musculature to provide significantly better clinical interventions and outcomes than the current practice.

Example 4

Figure 41:
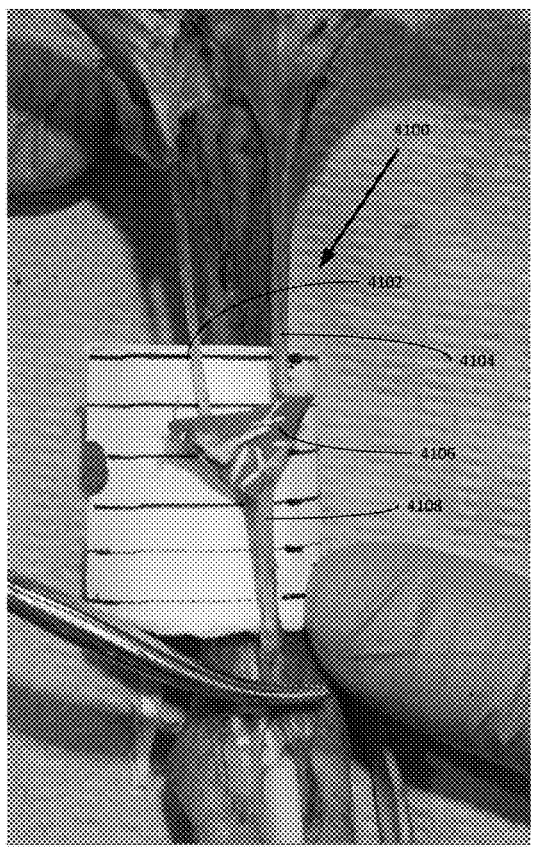
FIG. 41 is a photographic plan view of a triangular tendon insert implanted in a chicken cadaver to actuate foot movement.

This example demonstrates the ability to implant a triangular insert into a chicken cadaver foot. FIG. 41 shows a triangular insert, 4106, implanted in a chicken cadaver foot connecting the input tendon, 4108, to the two output tendons, 4104 and 4102. The input tendon was then actuated, which caused the output tendons to pull and raise the foot of the chicken.

Example 5

This example demonstrates the ability to implant a section of artificial tendon into a rat cadaver's tail in preparation for an in vivo experiment to determine whether the implant will cause significant irritation to the surrounding tissue and thus cause fibrosis.

Figure 42:
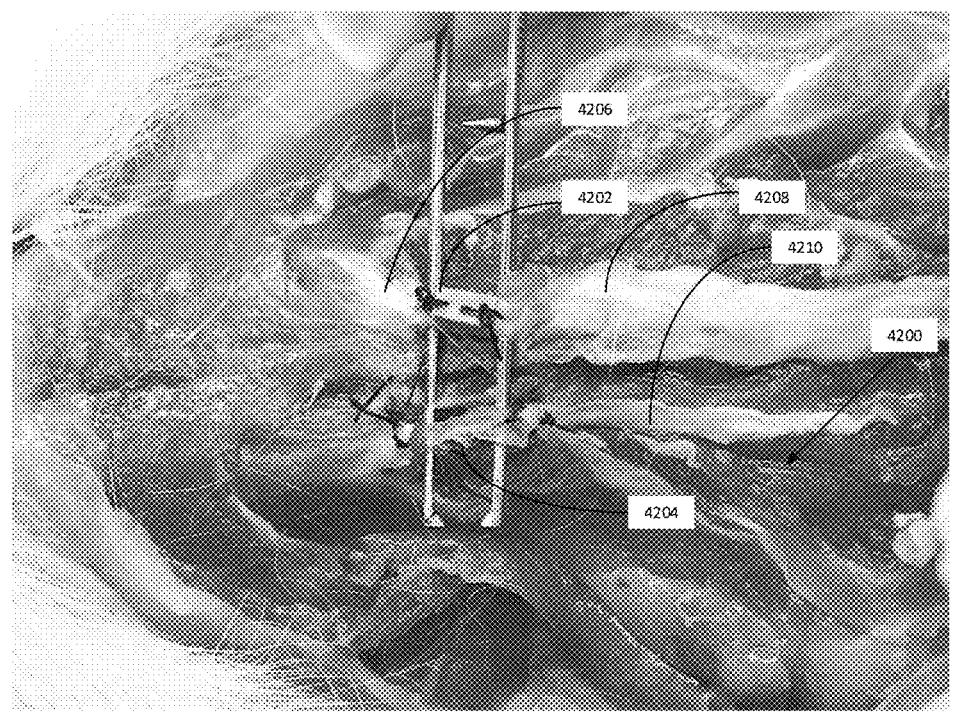
FIG. 42 is a photographic plan view of two artificial tendons implanted in line with biological tendons in the tail of a rat cadaver to provide left and right tail movement.

FIG. 42 shows the tail area musculature and tendons of a rat cadaver, wherein the major biological tendons 4210, 4206 connecting to the base of the tail have implanted lengths of artificial tendon 4202, 4204 in line with the input and output biological tendons.

Figure 43:
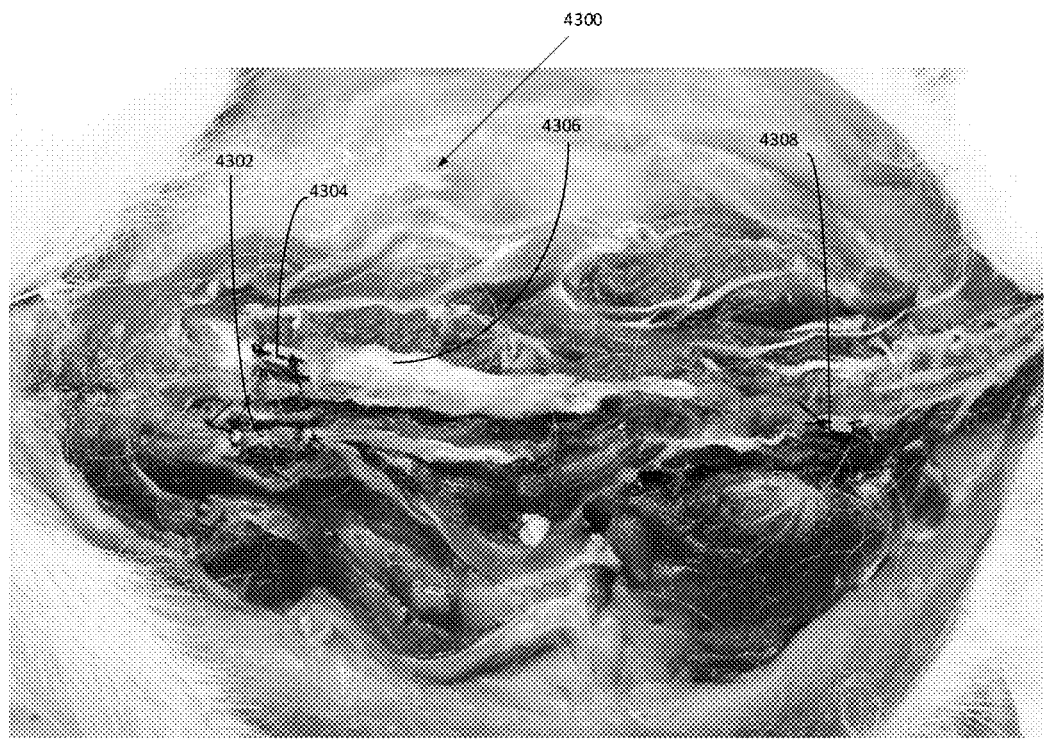
FIG. 43 is a plan view of multiple artificial tendons implanted in line with the biological tendons in the tail area of a rat cadaver to facilitate left and right tail movement.

FIG. 43 shows an expanded version of the tail area in FIG. 42 wherein a third artificial tendon implantation, 4308, is shown.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An implantable passive engineered mechanism, comprising a triangular insert having a first, second, and third vertices and first, second, and third sides, the first side having at least one aperture to receive sutures for coupling the first side to a tendon or tendons and the second side having at least one aperture to receive sutures for coupling the second side to a tendon or tendons.

2. A method, comprising using an implantable passive engineered mechanism according to claim 1.

3. The method according to claim 2 wherein the implantable passive engineered mechanism comprises a biocompatible implantable passive engineered mechanism.

4. The method of claim 2 wherein the implantable passive engineered mechanism comprises a polymeric material, a metal, an alloy, or combinations thereof.

5. An implantable passive engineered mechanism comprising at least one component configured to scale an input force or movement to at least one tendon or muscle coupled to the mechanism, the implantable passive engineered mechanism comprising a prosthetic soft tendon network for coupling to biological tendons, the soft tendon network having a first, second, and third side, and first, second, and third vertices, the first vertex being sutured to an input force and the second and third vertices being configured for anchoring to a bone and to output tendons.

6. The mechanism according to claim 5 comprising a biocompatible material.

7. The mechanism according to claim 5 wherein the implantable passive engineered mechanism comprises a polymeric material, a metal, an alloy, or combinations thereof.

8. The mechanism according claim 5 wherein the implantable passive engineered mechanism comprises a biocompatible material.

9. A method, comprising using an implantable passive engineered mechanism according to claim 5.

10. An implantable passive engineered mechanism comprising at least one component configured to scale an input force or movement to at least one tendon or muscle coupled to the mechanism, the implantable passive engineered mechanism comprising a pulley having a pulley body, a wheel rotatable about an axle, and a pulley cable wound about the wheel, the cable comprising a first end and a second end, wherein the first end of the pulley cable is effectively coupled to an input force, and the second end of the pulley cable and the pulley body are coupled to a bone.

11. A method, comprising using an implantable passive engineered mechanism according to claim 10.

12. An implantable passive engineered mechanism, comprising three levers arranged hierarchically, each lever having a first end and a second end, and wherein the first and second ends of the first lever are effectively coupled to the second and third levers, and the first and second ends of the second and third levers can be effectively coupled to output tendons, and wherein an input force is effectively coupled to the first lever at a position between the first and second end.

13. The mechanism according to claim 12 comprising a biocompatible material.

14. The mechanism according to claim 12 comprising a polymeric material, a metal, an alloy, or combinations thereof.

15. A method, comprising using an implantable passive engineered mechanism according to claim 12.

16. An implantable passive engineered mechanism, comprising a scissor mechanism having a first end and a second end and wherein the first end has a first portion configured for anchoring to a bone and a second portion configured to be received in a slot defined in a bone and wherein the second end has a first portion for coupling to an input force and the mechanism is configured to be effectively coupled to an output tendon at a position between the two ends.

17. The mechanism according to claim 16 comprising a biocompatible material.

18. The mechanism according to claim 16 comprising a polymeric material, a metal, an alloy, or combinations thereof.

19. A method, comprising using an implantable passive engineered mechanism according to claim 16.

* * * * *

UNITED STATES PATENT AND TRADEMARK OFFICE
CERTIFICATE OF CORRECTION

| | | |
|---|---|---|
| PATENT NO. | : 9,925,035 B2 | Page 1 of 1 |
| APPLICATION NO. | : 14/725971 | |
| DATED | : March 27, 2018 | |
| INVENTOR(S) | : Balasubramanian et al. | |

It is certified that error appears in the above-identified patent and that said Letters Patent is hereby corrected as shown below:

In the Specification

Column 1, Line 12, after the paragraph entitled CROSS REFERENCE TO RELATED APPLICATION and before the paragraph entitled FIELD, please add the following new paragraph:

--STATEMENT OF GOVERNMENT SUPPORT
This invention was made with government support under Award No. AR052345 awarded by the National Institutes of Health. The government has certain rights in the invention.--

Signed and Sealed this
Twenty-third Day of June, 2020

Andrei Iancu
*Director of the United States Patent and Trademark Office*